(12) United States Patent
Mullins et al.

(10) Patent No.: US 11,511,112 B2
(45) Date of Patent: Nov. 29, 2022

(54) WEARABLE MEDICAL DEVICE

(71) Applicant: BIOVISICS MEDICAL, INC., Delano, MN (US)

(72) Inventors: Brian Mullins, Minneapolis, MN (US); Dallas Erdahl, Minneapolis, MN (US); Russell Cluff, Minneapolis, MN (US); Peyman Pirzadeh, New Brighton, MN (US)

(73) Assignee: Biovisics Medical, Inc., Delano, MN (US)

( * ) Notice: Subject to any disclaimer, the term of this patent is extended or adjusted under 35 U.S.C. 154(b) by 0 days.

(21) Appl. No.: 16/900,115

(22) Filed: Jun. 12, 2020

(65) Prior Publication Data

US 2020/0391029 A1  Dec. 17, 2020

Related U.S. Application Data

(60) Provisional application No. 62/884,890, filed on Aug. 9, 2019, provisional application No. 62/861,658, filed on Jun. 14, 2019.

(51) Int. Cl.
*A61N 1/36* (2006.01)
*A61N 1/04* (2006.01)
*H02J 7/00* (2006.01)

(52) U.S. Cl.
CPC ....... *A61N 1/36046* (2013.01); *A61N 1/0452* (2013.01); *A61N 1/0456* (2013.01);
(Continued)

(58) Field of Classification Search
CPC .............. A61N 1/36046; A61N 1/3603; A61N 1/0452; A61N 1/0456; A61N 1/0492;
(Continued)

(56) References Cited

U.S. PATENT DOCUMENTS 2,283,752 A   5/1942  Gonsett
2,527,947 A   10/1950  Loos
(Continued)

FOREIGN PATENT DOCUMENTS

CN   1096460 A   12/1994
DE   202012003100 U1   10/2012
(Continued)

OTHER PUBLICATIONS

Invite to Pay Additional Fees dated Aug. 31, 2020 for International Application No. PCT/US2020/037458.
(Continued)

*Primary Examiner* — Carl H Layno
*Assistant Examiner* — Anh-Khoa N Dinh
(74) *Attorney, Agent, or Firm* — Seager, Tufte & Wickhem, LLP

(57) ABSTRACT

Wearable devices for providing therapy to a patient may include disposable or reusable treatment pads. The treatment pads may include electrodes and are configured to apply energy to various regions around the head and eyes. The treatment pads may provide therapy when the eyes are open or closed. The wearable device may include a battery and/or control circuitry for issuing therapy pulses through the electrodes.

16 Claims, 27 Drawing Sheets

(52) U.S. Cl.
CPC ......... *A61N 1/0492* (2013.01); *A61N 1/3603* (2017.08); *H02J 7/0013* (2013.01)

(58) Field of Classification Search
CPC ............ A61N 1/36021; A61N 1/36036; A61N 1/36039; A61N 1/36038; A61N 5/0618; A61N 2005/0648; A61N 1/0484; A61N 1/36135; H02J 7/0013; A61B 5/6803; A61B 3/113; A61B 5/163; A61B 5/378; A61B 3/00; A61B 3/101; A61B 5/1103; A61B 8/10

See application file for complete search history.

(56) References Cited

U.S. PATENT DOCUMENTS

| | | | |
|---|---|---|---|
| 2,760,483 A | 8/1956 | Tassicker | |
| 3,376,870 A | 4/1968 | Yamamoto et al. | |
| 3,669,119 A * | 6/1972 | Symmes | A61N 1/0408 600/26 |
| D246,529 S | 11/1977 | Willard | |
| 4,162,542 A | 7/1979 | Frank | |
| D280,670 S | 9/1985 | Fireman | |
| 4,551,149 A | 11/1985 | Scairra | |
| 4,614,193 A | 9/1986 | Liss et al. | |
| 4,628,933 A | 12/1986 | Michelson | |
| 4,664,117 A | 5/1987 | Beck | |
| 4,712,558 A | 12/1987 | Kidd et al. | |
| 4,979,811 A | 12/1990 | Boyer | |
| 5,024,223 A | 6/1991 | Chow | |
| 5,109,844 A | 5/1992 | De Juan et al. | |
| 5,147,284 A | 9/1992 | Fedorov et al. | |
| 5,154,174 A | 10/1992 | Hawlina | |
| 5,193,540 A | 3/1993 | Schulman et al. | |
| 5,263,200 A | 11/1993 | Miller | |
| 5,522,864 A | 6/1996 | Wallace et al. | |
| 5,556,423 A | 9/1996 | Chow et al. | |
| 5,597,381 A | 1/1997 | Rizzo, III | |
| 5,643,330 A | 7/1997 | Holsheimer et al. | |
| 5,836,996 A | 11/1998 | Doorish | |
| 5,843,147 A | 12/1998 | Testerman et al. | |
| 5,865,839 A | 2/1999 | Doorish | |
| 5,873,901 A | 2/1999 | Wu et al. | |
| 5,895,415 A | 4/1999 | Chow et al. | |
| 5,935,155 A | 8/1999 | Humayun et al. | |
| 5,944,747 A | 8/1999 | Greenberg et al. | |
| 6,007,532 A | 12/1999 | Netherly | |
| D421,124 S | 2/2000 | Yavitz | |
| 6,035,236 A | 3/2000 | Jarding et al. | |
| D425,623 S | 5/2000 | Funk | |
| D429,817 S | 8/2000 | Banks | |
| 6,101,411 A | 8/2000 | Newsome | |
| 6,131,208 A | 10/2000 | Banks | |
| 6,154,671 A | 11/2000 | Parel et al. | |
| D440,660 S | 4/2001 | Sternberg | |
| 6,230,057 B1 | 5/2001 | Chow et al. | |
| D444,561 S | 7/2001 | Stein | |
| 6,275,735 B1 | 8/2001 | Jarding et al. | |
| 6,282,449 B1 | 8/2001 | Kamerling et al. | |
| 6,306,075 B1 | 10/2001 | Shadduck | |
| 6,324,429 B1 | 11/2001 | Shire et al. | |
| 6,389,317 B1 | 5/2002 | Chow et al. | |
| 6,400,989 B1 | 6/2002 | Eckmiller | |
| 6,408,211 B1 | 6/2002 | Powell | |
| 6,424,864 B1 | 7/2002 | Matsuura | |
| 6,442,431 B1 | 8/2002 | Veraart et al. | |
| 6,458,157 B1 | 10/2002 | Suaning | |
| 6,515,227 B1 | 2/2003 | Massey et al. | |
| 6,549,808 B1 * | 4/2003 | Gisel | A61N 1/36046 607/53 |
| 6,611,716 B2 | 8/2003 | Chow et al. | |
| 6,755,530 B1 | 6/2004 | Loftus et al. | |
| 6,792,314 B2 | 9/2004 | Byers et al. | |
| 6,976,998 B2 | 12/2005 | Rizzo et al. | |
| 6,990,377 B2 | 1/2006 | Gliner et al. | |
| 7,001,608 B2 | 2/2006 | Fishman et al. | |
| 7,003,354 B2 | 2/2006 | Chow et al. | |
| 7,006,873 B2 | 2/2006 | Chow et al. | |
| 7,031,776 B2 | 4/2006 | Chow et al. | |
| 7,037,943 B2 | 5/2006 | Peyman | |
| 7,043,308 B2 | 5/2006 | Cohen | |
| 7,047,080 B2 | 5/2006 | Palanker et al. | |
| 7,058,455 B2 | 6/2006 | Huie, Jr. et al. | |
| 7,067,327 B2 | 6/2006 | Wu et al. | |
| 7,130,693 B1 | 10/2006 | Montalbo | |
| 7,139,612 B2 | 11/2006 | Chow et al. | |
| 7,146,209 B2 | 12/2006 | Gross et al. | |
| 7,147,865 B2 | 12/2006 | Fishman et al. | |
| 7,158,834 B2 | 1/2007 | Paul, Jr. | |
| 7,158,836 B2 | 1/2007 | Suzuki | |
| 7,248,928 B2 | 7/2007 | Yagi | |
| 7,251,528 B2 | 7/2007 | Harold | |
| 7,306,621 B1 | 12/2007 | Halla et al. | |
| 7,321,796 B2 | 1/2008 | Fink et al. | |
| 7,337,008 B2 | 2/2008 | Terasawa et al. | |
| 7,398,124 B2 | 7/2008 | Fujikado et al. | |
| 7,400,021 B2 | 7/2008 | Wu et al. | |
| 7,447,547 B2 | 11/2008 | Palanker | |
| 7,447,548 B2 | 11/2008 | Eckmiller | |
| 7,458,456 B2 | 12/2008 | Hogan et al. | |
| 7,556,621 B2 | 7/2009 | Palanker et al. | |
| 7,877,148 B2 | 1/2011 | Chowdhury et al. | |
| 7,883,535 B2 | 2/2011 | Cantin et al. | |
| 7,974,699 B2 | 7/2011 | Tano et al. | |
| 7,979,134 B2 | 7/2011 | Chow et al. | |
| 7,981,062 B2 | 7/2011 | Chow et al. | |
| 3,000,804 A1 | 8/2011 | Wessendorf et al. | |
| 8,039,445 B2 | 10/2011 | Behar-Cohen et al. | |
| 8,070,688 B2 | 12/2011 | Livne et al. | |
| 8,190,266 B2 | 5/2012 | Ameri et al. | |
| 8,197,539 B2 | 6/2012 | Nasiatka et al. | |
| 8,260,428 B2 | 9/2012 | Fink et al. | |
| 8,265,764 B2 | 9/2012 | Tano et al. | |
| 8,306,626 B2 | 11/2012 | Chow et al. | |
| 8,377,120 B2 | 2/2013 | Lipshitz et al. | |
| 8,396,561 B2 | 3/2013 | Pezaris et al. | |
| 8,396,562 B2 | 3/2013 | Ameri et al. | |
| 8,398,692 B2 | 3/2013 | Deisseroth et al. | |
| 8,433,417 B2 | 4/2013 | Flood | |
| 8,478,415 B1 | 7/2013 | Halla et al. | |
| 8,515,548 B2 | 8/2013 | Rofougaran et al. | |
| 8,612,002 B2 | 12/2013 | Faltys et al. | |
| 8,634,923 B2 | 1/2014 | Sharpee et al. | |
| 8,639,345 B2 | 1/2014 | Eipper et al. | |
| 8,691,877 B2 | 4/2014 | Fun et al. | |
| 8,700,167 B2 | 4/2014 | Sabel | |
| 8,725,266 B2 | 5/2014 | Olson et al. | |
| 8,731,683 B2 | 5/2014 | Lindenthaler | |
| 8,734,513 B2 | 5/2014 | Wu et al. | |
| 8,771,349 B2 | 7/2014 | Schachar | |
| 8,788,041 B2 | 7/2014 | Yun et al. | |
| 8,801,942 B2 | 8/2014 | Scorsone et al. | |
| 8,824,156 B2 | 9/2014 | Tai et al. | |
| 8,852,290 B2 | 10/2014 | Rowley et al. | |
| 8,864,805 B2 | 10/2014 | Deisseroth et al. | |
| 8,868,202 B2 | 10/2014 | Della Santina et al. | |
| 8,903,495 B2 | 12/2014 | Greenberg et al. | |
| 8,909,340 B2 | 12/2014 | Yun | |
| 8,918,186 B2 | 12/2014 | Tiedtke | |
| 8,918,188 B2 | 12/2014 | Tiedtke | |
| 8,972,004 B2 | 3/2015 | Simon et al. | |
| 9,002,463 B2 | 4/2015 | Tiedtke | |
| 9,037,251 B2 | 5/2015 | Narayan et al. | |
| 9,037,252 B2 | 5/2015 | Tiedtke | |
| 9,037,255 B2 | 5/2015 | Rocke et al. | |
| 9,078,743 B2 | 7/2015 | Tai et al. | |
| 9,079,042 B2 | 7/2015 | Tiedtke et al. | |
| 9,125,734 B2 | 9/2015 | Keller et al. | |
| 9,144,608 B2 | 9/2015 | Olson et al. | |
| 9,162,060 B2 | 10/2015 | Wrobel et al. | |
| 9,162,061 B2 | 10/2015 | Barnes | |
| 9,180,309 B2 | 11/2015 | Nirenberg et al. | |
| 9,186,523 B1 | 11/2015 | Zolli | |
| 9,187,745 B2 | 11/2015 | Deisseroth et al. | |

(56) References Cited

U.S. PATENT DOCUMENTS

| | | | |
|---|---|---|---|
| 9,199,080 B2 | 12/2015 | Gekeler et al. | |
| 9,220,634 B2 | 12/2015 | Nirenberg | |
| 9,220,894 B1 | 12/2015 | Zhu | |
| 9,233,026 B2 | 1/2016 | Ziemeck et al. | |
| 9,233,258 B2 | 1/2016 | Simon et al. | |
| 9,242,067 B2 | 1/2016 | Shore et al. | |
| 9,403,001 B2 | 1/2016 | Simon et al. | |
| 9,302,103 B1 | 4/2016 | Nirenberg | |
| 9,322,713 B2 | 4/2016 | Narayan et al. | |
| 9,326,887 B2 | 5/2016 | Yun | |
| 9,339,650 B2 | 5/2016 | Rezai et al. | |
| 9,345,568 B2 | 5/2016 | Cho et al. | |
| 9,370,348 B2 | 6/2016 | Tally et al. | |
| 9,381,355 B2 | 7/2016 | Khraiche et al. | |
| 9,452,289 B2 | 9/2016 | Chichilnisky et al. | |
| 9,456,836 B2 | 10/2016 | Boling et al. | |
| 9,468,760 B1 | 10/2016 | Lin | |
| 9,498,380 B2 | 11/2016 | Berdahl et al. | |
| 9,630,013 B2 | 4/2017 | Bachinski et al. | |
| 9,636,212 B2 | 5/2017 | Tiedtke et al. | |
| 9,682,232 B2 | 6/2017 | Shore et al. | |
| 9,687,652 B2 | 6/2017 | Franke et al. | |
| 9,697,746 B2 | 7/2017 | Barnes et al. | |
| 9,737,710 B2 | 8/2017 | Fan | |
| 9,737,711 B2 | 8/2017 | Twyford et al. | |
| 9,789,312 B2 | 10/2017 | Fukuma et al. | |
| 9,795,787 B2 | 10/2017 | Cho et al. | |
| 9,821,003 B2 | 11/2017 | Fun | |
| 9,821,159 B2 | 11/2017 | Ackermann et al. | |
| 9,844,459 B2 | 12/2017 | Badawi | |
| 9,867,988 B2 | 1/2018 | Fink et al. | |
| 9,884,180 B1 | 2/2018 | Ho et al. | |
| 9,895,529 B2 | 2/2018 | Tiedtke | |
| 9,925,373 B2 | 3/2018 | Nirenberg | |
| 9,931,506 B2 | 4/2018 | Chung et al. | |
| 9,937,346 B2 | 4/2018 | Lineaweaver et al. | |
| 9,950,153 B2 | 4/2018 | Wagner et al. | |
| 9,956,425 B2 | 5/2018 | Peyman | |
| 9,962,540 B2 | 5/2018 | Picaud et al. | |
| 9,962,558 B2 | 5/2018 | Peyman | |
| 9,980,388 B2 | 5/2018 | Tai et al. | |
| 9,990,861 B2 | 6/2018 | Chichilnisky et al. | |
| 10,010,364 B2 | 7/2018 | Harrington | |
| 10,071,251 B2 | 9/2018 | Bachinski et al. | |
| 10,112,048 B2 | 10/2018 | Franke et al. | |
| 10,129,647 B2 | 11/2018 | Seo et al. | |
| 10,347,050 B1 | 7/2019 | Wang et al. | |
| 2003/0158588 A1 | 8/2003 | Rizzo et al. | |
| 2003/0233135 A1 | 12/2003 | Yee | |
| 2003/0233137 A1 | 12/2003 | Paul, Jr. | |
| 2004/0106965 A1 | 6/2004 | Chow | |
| 2004/0176820 A1 | 9/2004 | Paul, Jr. | |
| 2005/0004625 A1 | 1/2005 | Chow | |
| 2005/0049578 A1 | 3/2005 | Tu et al. | |
| 2005/0137649 A1 | 6/2005 | Paul | |
| 2006/0142818 A1 | 6/2006 | Chow et al. | |
| 2006/0167524 A1* | 7/2006 | Kimura | A61N 1/0472 607/45 |
| 2007/0093877 A1 | 4/2007 | Beecham et al. | |
| 2007/0179564 A1 | 8/2007 | Harold | |
| 2008/0171929 A1 | 7/2008 | Katims | |
| 2008/0194531 A1 | 8/2008 | Steer et al. | |
| 2009/0217938 A1 | 9/2009 | Rabe et al. | |
| 2009/0287276 A1 | 11/2009 | Greenberg et al. | |
| 2011/0081333 A1 | 4/2011 | Shantha et al. | |
| 2012/0123501 A1 | 5/2012 | Greenberg et al. | |
| 2013/0053733 A1 | 2/2013 | Korb et al. | |
| 2013/0066396 A1 | 3/2013 | Gekeler et al. | |
| 2013/0184782 A1 | 7/2013 | Eipper et al. | |
| 2014/0257433 A1 | 9/2014 | Ackermann et al. | |
| 2014/0277435 A1 | 9/2014 | Gefen | |
| 2014/0324147 A1 | 10/2014 | Wagner | |
| 2015/0018927 A1* | 1/2015 | Warschewske | A61N 1/0408 600/26 |
| 2015/0039067 A1 | 2/2015 | Greenberg et al. | |
| 2015/0209174 A1 | 7/2015 | Abreu | |
| 2016/0051439 A1 | 2/2016 | Brown et al. | |
| 2016/0317474 A1 | 11/2016 | Aung et al. | |
| 2017/0266445 A1 | 9/2017 | O'Clock | |
| 2018/0064935 A1 | 3/2018 | Leonhardt et al. | |
| 2018/0228237 A1 | 8/2018 | Zhang et al. | |
| 2018/0318585 A1 | 11/2018 | Pfeifer | |
| 2018/0318586 A1 | 11/2018 | Salazar | |
| 2019/0143116 A1 | 5/2019 | Mowery et al. | |

FOREIGN PATENT DOCUMENTS

| | | | |
|---|---|---|---|
| EP | 1985332 A1 | 10/2008 | |
| GB | 2246709 A * | 2/1992 | ......... A61N 1/36014 |
| GB | 2246709 A | 2/1992 | |
| WO | 2006086452 A1 | 8/2006 | |
| WO | 2013124141 A1 | 8/2013 | |
| WO | 2015095257 A2 | 6/2015 | |
| WO | 2016089751 A1 | 6/2016 | |
| WO | 2017048731 A1 | 3/2017 | |
| WO | 2017064500 A1 | 4/2017 | |
| WO | 2018013835 A1 | 1/2018 | |
| WO | WO-2018102778 A1 * | 6/2018 | ........... A61N 1/0492 |
| WO | 2018129351 A1 | 7/2018 | |
| WO | 2018208009 A1 | 11/2018 | |

OTHER PUBLICATIONS

Schatz et al; "Transcorneal Electrical Stimulation for Patients with Retinitis Pigmentosa: A Prospective Randomized, Sham-Controlled Follow-Up Study Over 1 Year", Investigative Ophthalmology and Visual Science, vol. 58, No. 1, pp. 257-269, 2017. Accessed on Sep. 25, 2018.

Scyfix SF700 Manual, Instructions for Use, pp. 1-28, Scyfix LLC.

International Search Report and Written Opinion dated Jul. 10, 2020 for International Application No. PCT/JS2020/027438.

Chlaihawi et al.; "Development of Printed and Flexible Dry ECG Electrodes", Sensing and Bio-Sensing Research, vol. 20, pp. 9-15, 2018.

2019 World Congress Eye and Chip Speaker Abstracts, pp. 20-54, 2019.

Gall et al; Alternating Current Stimulation for Vision Restoration after Optic Nerve Damage: A Randomized Clinical Trial, PLOS One, pp. 1-13, 2016, accessed Nov. 12, 2018.

Chow et al; "The Artificial Silicon Retina in Retinitis Pigmentosa Patients", Trans Am Ophthalmol Soc., vol. 108, pp. 120-154, 2010.

Dawson et al; "Improved Electrode for Electroretinography," Invest. Ophthalmol. Visual Sci. vol. 8, No. 9, pp. 988-991, Sep. 1979, accessed on May 2, 2019.

Diagnosys DTL Brochure, Diagnosys, LLC, 2016, Accessed Nov. 20, 2017.

DTL Installation, Diagnosys LLC, Accessed Oct. 6, 2020.

Bittner et al; "Longevity of Visual Improvements following Transcorneal Electrical Stimulation and Efficacy of Retreatment in Three Individuals with Retinitis Pigmentosa", Graefe's Archive for Clinical and Experimental Ophthalmology, 2017, Published online on Dec. 8, 2017.

H110002B Summary of Safety and Probable Benefits, Second Sight Medical Products Inc., issued Dec. 11, 2001.

H110002C Second Sight Manuals, Second Sight Medical Products Inc., 2013.

Naycheva et al; Phosphene Thresholds Elicited by Trasncomeal Electrical Stimulation in Healthy Subjects and Patients with Retinal Disease, Investigative Ophthamology and Visual Science, vol. 53, No. 12, pp. 7440-7448, 2012, accessed on Sep. 20, 2018.

Schatz et al; "Transcorneal Electrical Stimulation for Patients with Retinitis Pigmentosa: A Prospective Randomized, Sham-Controlled Follow-Up Study Over 1 Year", Investigative Ophthalmology and Visual Science, vol. 58, No. 1, pp. 257-269, 2017. Accessed on Sep. 25, 2018.

Scyfix SF700 Manual, Instructions for Use, pp. 1-28, Scyfix LLC, Mar. 3, 2004.

(56) References Cited

OTHER PUBLICATIONS

Stauffer et al; "Skin Conformal Polymer Electrodes for Clinical ECG and EEG Recordings," Advanced Healthcare Materials pp. 1-10, 2018.
Manthey et al; "Using Electrical Stimulation to Enhance the Efficacy of Cell Transplantation Therapies for Neurodegenerative Retinal Diseases: Concepts, Challenges, and Future Perspectives", Cell Transplantation, vol. 26, pp. 949-965, 2017.
Invitation to Pay Additional Fees dated Dec. 17, 2019 for International Application No. PCT/US2019/054028.
Invitation to Pay Additional Fees dated Feb. 14, 2020 for International Application No. PCT/US2019/063580.
International Search Report and Written Opinion dated Jul. 10, 2020 for International Application No. PCT/US2020/027438.

\* cited by examiner

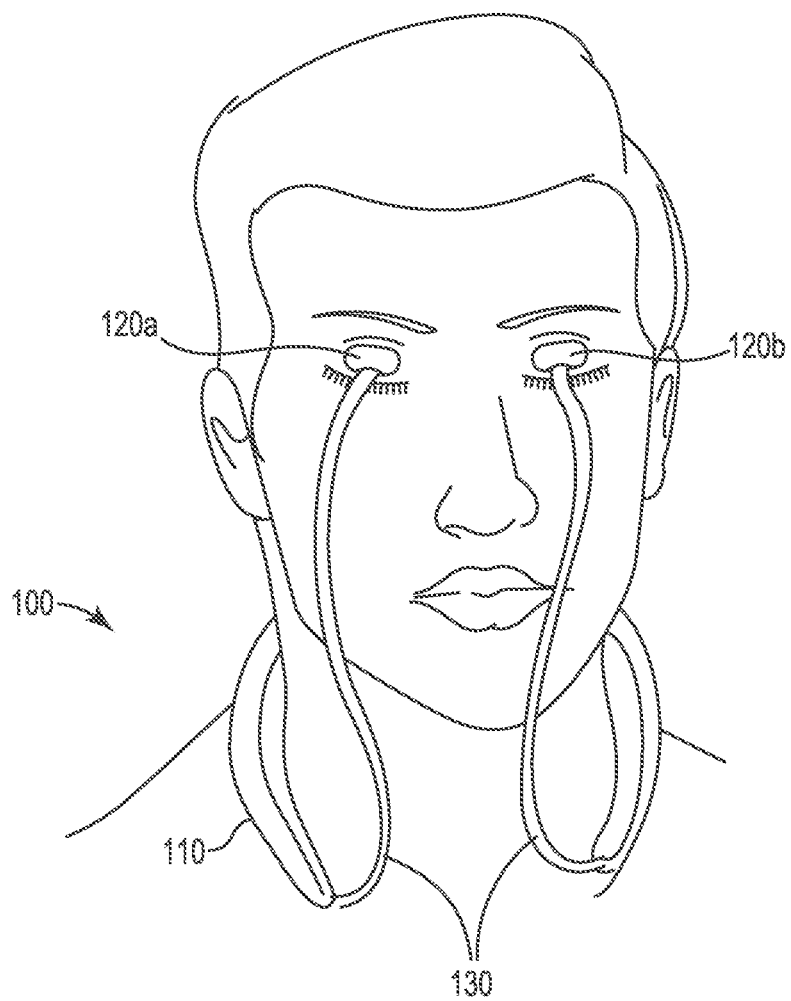

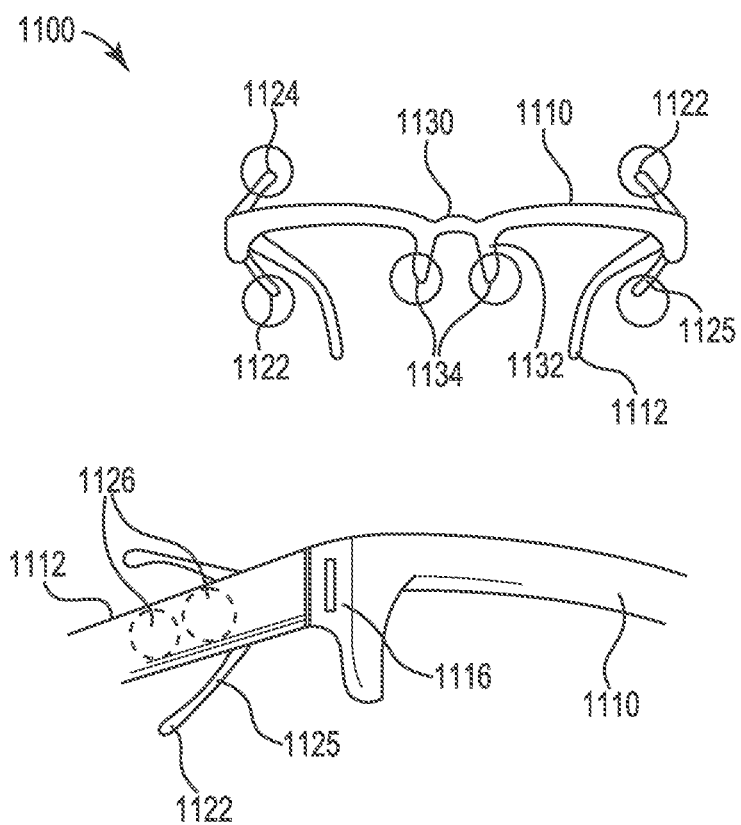

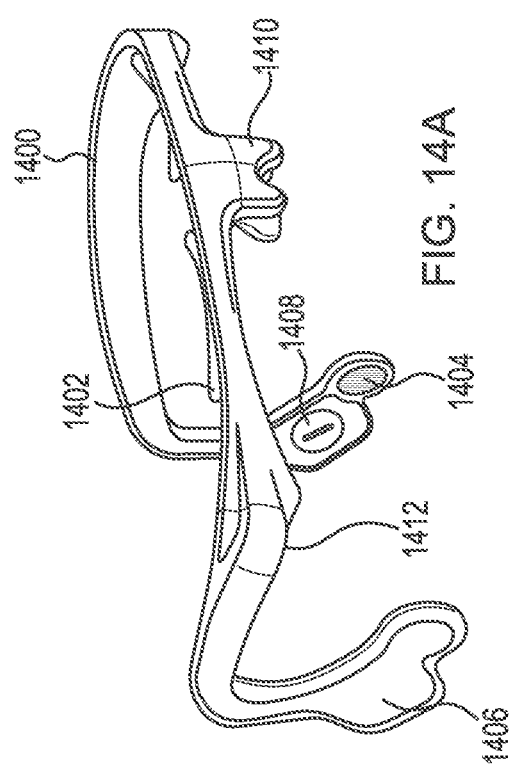
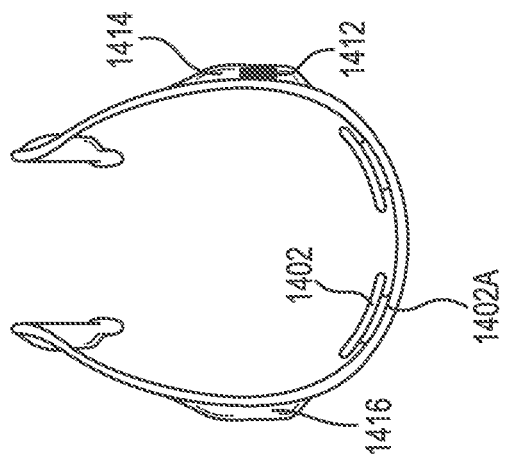
FIG. 14A
FIG. 14B

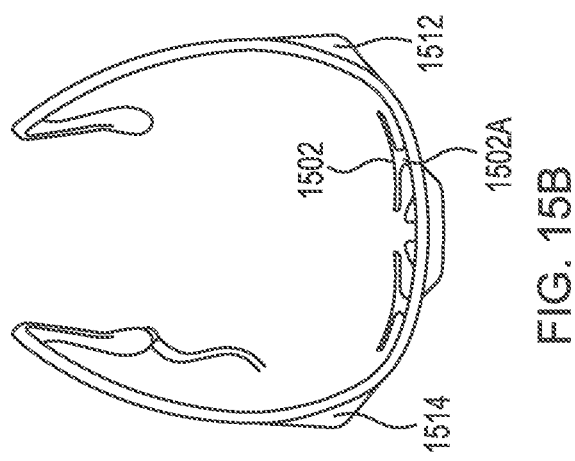
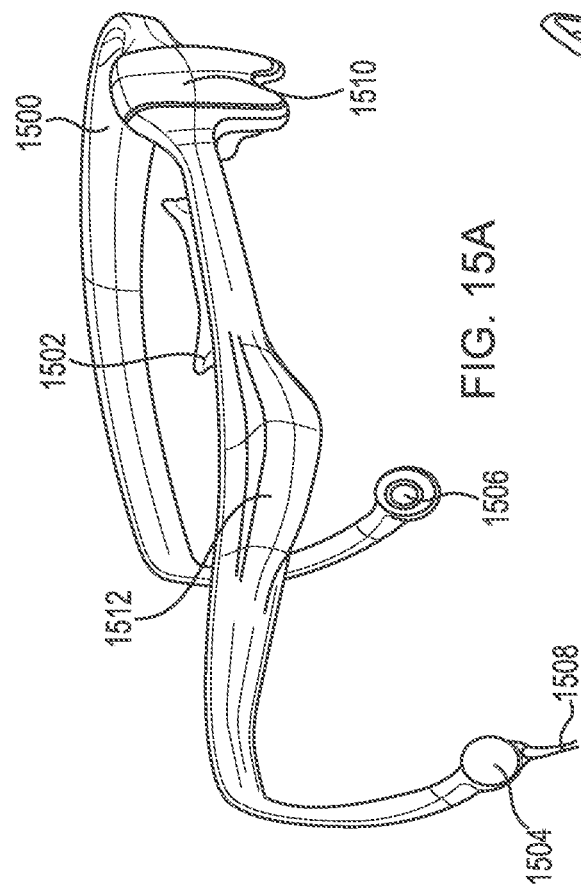

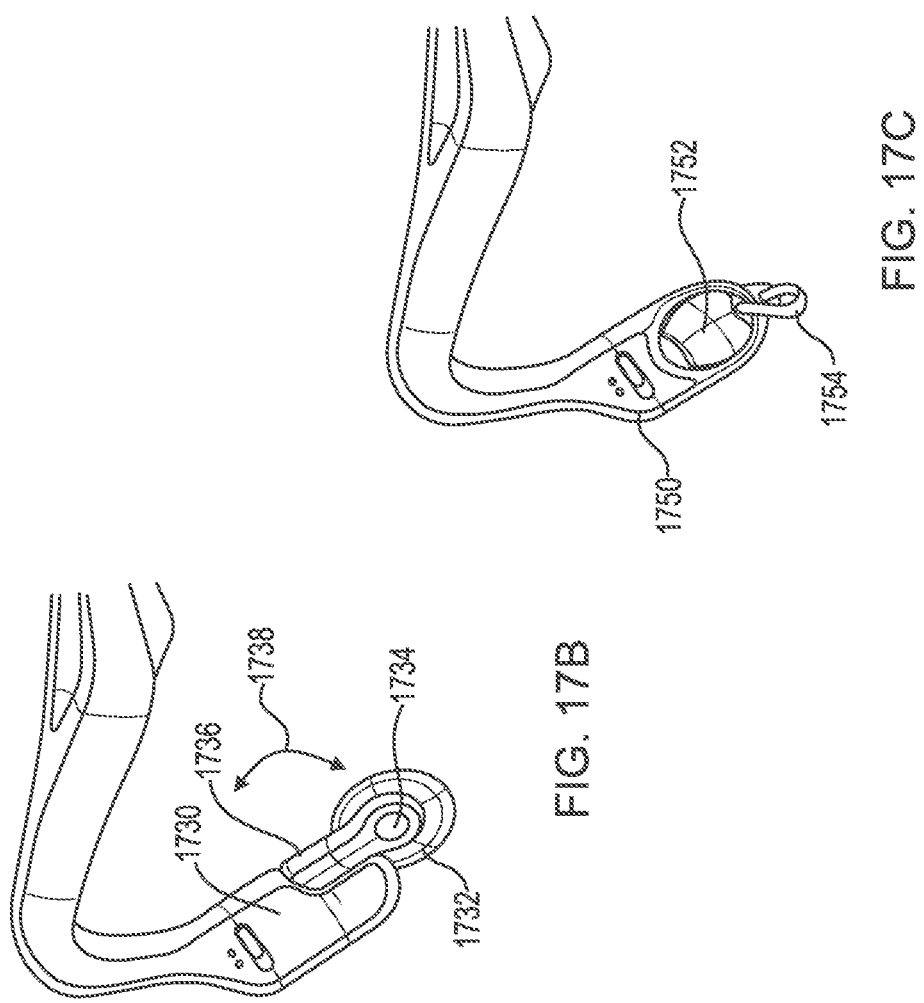

WEARABLE MEDICAL DEVICE

CROSS REFERENCE TO RELATED APPLICATIONS

The present application claims the benefit of and priority to U.S. Provisional Patent Application Ser. No. 62/884,890, filed Aug. 9, 2019, titled WEARABLE MEDICAL DEVICE, and also claims the benefit of and priority to U.S. Provisional Patent Application Ser. No. 62/861,658, filed Jun. 14, 2019, and titled WEARABLE MEDICAL DEVICE, the disclosures of which are incorporated herein by reference.

TECHNICAL FIELD

The disclosure pertains to medical devices and more particularly to wearable medical devices for treating or diagnosing areas of the body including the eyes and head, and methods for using such medical devices.

BACKGROUND

A wide variety of medical devices have been developed for medical use including, for example, medical devices utilized to treat or gather diagnostic information for medical conditions of the eye and head. These medical devices may be used to provide therapy, such as electrotherapy or to gather information from various regions including the eyes and brain. Of the known medical devices and methods, each has certain advantages and disadvantages. There is an ongoing need to provide alternative medical devices as well as alternative methods for manufacturing and using the medical devices.

SUMMARY

The present inventors have recognized a need for new and alternative designs for electrical therapy systems, particularly those configured to issue electrical therapy direct to the structures and tissues in and around the eye including, for example and without limitation, neural, vascular, muscle and other tissue. A variety of particular uses for such therapy, and further alternatives, are described in greater detail below. For example, in some examples therapy may include both electrical and other modality of therapy, or electrotherapy in addition to biologic, drug, transplantation, etc. Aims and benefits may include, for example and without limitation, greater or enhanced comfort, wearability, the ability to engage in non-therapy activity while receiving therapy, predictability and repeatability of therapy itself, and/or simplicity, though not each embodiment described herein will accomplish each such aim.

An illustrative and non-limiting example takes the form of a wearable device for providing therapy to a patient, the device comprising: a frame having a front piece and first and second arms extending therefrom, the front piece including a nosepiece, the first and second arms extending from the front piece to first and second earpieces, respectively, which are shaped to contact and rest, at least partly, on the ear of a user; at least one front electrode or electrode pad carried on the front piece; and at least one earpiece electrode carried on at least one of the earpieces.

Additionally or alternatively, the wearable device further comprises a power source and a control circuit coupled to the power source, the control circuit configured to issue electrical signals through the front electrode or front electrode pad and the earpiece electrode to provide therapy to the eye of a user. Additionally or alternatively, the power source may be either a rechargeable battery or a replaceable battery. Additionally or alternatively, the control circuit is contained in the first earpiece, and the power source is contained in the second earpiece. Additionally or alternatively, the front piece comprises a first expanded portion and a second expanded portion on either side of the nosepiece, the control circuit being contained in the first expanded portion and the power source being contained in the second expanded portion. Additionally or alternatively, the control circuit is contained in the nose piece. Additionally or alternatively, the power source is contained in the nose piece. Additionally or alternatively, the at least one front electrode or electrode pad is coupled to the front piece by an electrode carrier configured to place the at least one front electrode or electrode pad against the forehead of the user when worn. Additionally or alternatively, the at least one front electrode or electrode pad is coupled to the front piece by an electrode carrier configured to place the at least one front electrode or electrode pad against the upper eyelid of the user when worn.

Additionally or alternatively, the at least one front electrode is adjustable or moveable relative to the head of the user. Additionally or alternatively, the at least one front electrode is adjustable or moveable relative to the frame. Additionally or alternatively, the at least one front electrode is coupled to a spring to facilitate contact with the patient's skin. Additionally or alternatively, the at least one front electrode is carried on a pivoting or swivel prong or arm. Additionally or alternatively, the wearable device may be further characterized by the omission of any electrode on the face of the user below the palpebral aperture.

Additionally or alternatively, the first and second earpieces are detachable. Additionally or alternatively, the first and second earpieces are shaped to at least partly wrap around the ears of the user. Additionally or alternatively, the earpiece electrode is held on a flexible or moveable arm. Additionally or alternatively, the front piece is configured to receive first and second lenses. Additionally or alternatively, the wearable device may further include an on/off switch actuatable by a user carried on one of the first and second earpieces.

Another illustrative and non-limiting example takes the form of a wearable device for providing therapy to a patient, the device comprising: a frame having a front piece and first and second arms extending therefrom, the front piece including a nosepiece, the first and second arms extending from the front piece to first and second earpieces, respectively, which are shaped to contact and rest, at least partly, on the ear of a user; at least one front electrode or electrode pad carried on the front piece, the at least one front electrode being sized and shaped for placement on the upper eyelid of a user.

Additionally or alternatively, the wearable device may further comprise a power source and a control circuit coupled to the power source, the control circuit configured to issue electrical signals through the front electrode or front electrode pad to provide therapy to the eye of a user. Additionally or alternatively, the control circuit is contained in the first earpiece, and the power source is contained in the second earpiece. Additionally or alternatively, the front piece comprises a first expanded portion and a second expanded portion on either side of the nosepiece, the control circuit being contained in the first expanded portion and the power source being contained in the second expanded portion. Additionally or alternatively, the control circuit is contained in the nose piece. Additionally or alternatively, the power source is contained in the nose piece.

Additionally or alternatively, the at least one front electrode is adjustable or moveable relative to the head of the user. Additionally or alternatively, the at least one front electrode is adjustable or moveable relative to the frame. Additionally or alternatively, the at least one front electrode is coupled to a spring to facilitate contact with the patient's upper eyelid. Additionally or alternatively, the at least one front electrode is carried on a pivoting or swivel prong or arm.

Additionally or alternatively, the wearable device may be further characterized by the omission of any electrode on the face of the user below the palpebral aperture.

Additionally or alternatively, the wearable device may further comprise at least one earpiece electrode carried on at least one of the earpieces.

Additionally or alternatively, the at least one front electrode is configured for placement on the eyelid of the user by having a length in the range of about 1 to about 40 mm, and a width of about 1 to about 10 mm.

Additionally or alternatively, the at least one front electrode is configured for placement on the eyelid of the user by having a length in the range of about 10 to about 20 mm, and a width of about 2 to about 5 mm.

Still another illustrative and non-limiting example takes the form of a wearable device for providing therapy to a patient, the device comprising: a frame having a front piece and first and second arms extending therefrom, the front piece including a nosepiece, the first and second arms extending from the front piece to first and second earpieces, respectively, which are shaped to contact and rest, at least partly, on the ear of a user; and at least one nosepiece electrode carried on the nosepiece.

Additionally or alternative, the wearable device may further comprise at least one second electrode and a moveable or pivotable arm coupled to the frame, the arm carrying the at least one second electrode in a position such that, when the frame is worn by a user, the arm can be moved or pivoted to bring the at least one second electrode into contact with the temple of the user. Additionally or alternatively, the wearable device may further comprise at least one second electrode and an electrode carrier coupled to the front piece, the electrode carrier carrying the at least one second electrode in an adjustable manner such that, when the frame is worn by a user, the at least one second electrode is positioned on the forehead of the user. Additionally or alternatively, the wearable device may further comprise at least one second electrode and an electrode carrier coupled to the front piece, the electrode carrier carrying the at least one second electrode in an adjustable manner such that, when the frame is worn by a user, the at least one second electrode is positioned on an upper eyelid of the user. Additionally or alternatively, the wearable device may further comprise at least one second electrode coupled to at least one of the earpieces. Additionally or alternatively, the wearable device may further comprise a power source and a control circuit coupled to the power source, the control circuit configured to issue electrical signals between the nosepiece electrode and the at least one second electrode. Additionally or alternatively, the wearable device may further comprise a power source and a control circuit coupled to the power source, the control circuit configured to issue electrical signals via the nosepiece electrode to deliver therapy to the eye of the user. Additionally or alternatively, the control circuit is contained in the first earpiece, and the power source is contained in the second earpiece. Additionally or alternatively, the front piece comprises a first expanded portion and a second expanded portion on either side of the nosepiece, the control circuit being contained in the first expanded portion and the power source being contained in the second expanded portion. Additionally or alternatively, the control circuit is contained in the nose piece. Additionally or alternatively, the power source is contained in the nose piece.

Additionally or alternatively, the nosepiece electrode has a size in the range of about 1 to about 20 mm in length, and about 1 to about 20 mm in width.

Additionally or alternatively, the nosepiece electrode has a size in the range of about 4 to about 8 mm in width, and about 8 to about 15 mm in length.

Yet another illustrative and non-limiting example takes the form of a wearable device for providing therapy to a patient, the device comprising: a housing configured to extend at least partially around the patient's neck; at least one treatment pad configured to provide therapy to an eye of the patient, the treatment pad including at least one electrode and a connector electrically connecting the electrode on the treatment pad to the housing; and wherein the housing includes a compartment configured to receive the treatment pad when not in use.

Additionally or alternatively, the housing further includes a return electrode configured to contact skin on the patient's neck when the housing is disposed around the patient's neck. Additionally or alternatively, the housing contains control circuitry configured to generate electrical pulses to output via at least the at least one electrode on the at least one treatment pad, and a power source for providing electrical power to the control circuitry. Additionally or alternatively, the connector is retractable into the housing to thereby draw the at least one treatment pad into the compartment.

Another illustrative and non-limiting example takes the form of a wearable device assembly for providing therapy to a patient, the assembly comprising: at least one treatment pad having an electrode configured to provide therapy to an eye of a patient; a controller containing circuitry electrically connected to the treatment pad; and a battery; wherein the at least one treatment pad comprises a chamber for receiving the battery therein.

Additionally or alternatively, the battery is rechargeable, and the device further comprises a charging unit for charging the rechargeable battery while it is in the treatment pad. Additionally or alternatively, the at least one treatment pad includes first and second treatment pads configured to provide therapy to both eyes, wherein the wearable device assembly further includes a return electrode configured to be placed on the patient's temple, neck, back, shoulder, back of hand, arm, behind an ear, back, or chest. Additionally or alternatively, the at least one treatment pad has a soft but resilient perimeter adapted to match the shape of a patient's eye socket and to aid in retaining the at least one treatment pad in position once placed on the patient's eye.

Another illustrative and non-limiting example takes the form of a wearable device for providing therapy to a patient, the device comprising: first and second treatment pads each including an electrode configured to provide therapy to the patient's eyes; a frame configured to be worn on the patient's face as eyeglasses, the frame including two earpieces configured to extend along sides of the patient's face and over the patient's ears, and a bridge extending between the two earpieces and over the patient's nose bridge, the frame including first and second engagement members each configured to engage one of the first and second treatment pads; and an adjustment member disposed on each earpiece of the frame and configured to adjust a position of each treatment pad.

Additionally or alternatively, the adjustment member takes the form of a screw, and the adjustment member is adapted to move a treatment pad relative to the frame to adjust the treatment pad position on the patient when the frame is being worn.

Still another illustrative and non-limiting example takes the form of a wearable device for providing therapy to a patient, the device comprising: first and second treatment pads each including an electrode configured to provide therapy to the patient's eyes; a frame configured to hold the first and second treatment pads in a rotatable or sliding engagement; and a head strap coupled to the frame and configured to secure the frame to the patient's face with the first and second treatment pads in contact with the patient's eyes.

Another illustrative and non-limiting example takes the form of a wearable device for providing therapy to a patient, the device comprising: a mask configured to be worn on the patient's face, with first and second openings for the patient's eyes; and at least one electrode disposed on the mask adjacent one of the first and second openings, each electrode configured to provide therapy to one of the patient's eyes.

Another illustrative and non-limiting example takes the form of a wearable device for providing therapy to a patient, the device comprising: at least one disposable treatment patch each including at least one electrode configured to provide therapy to the patient's eyes, the treatment patch configured to conform to contours of the patient's face; and a frame configured to be worn on the patient's face as eyeglasses, the frame including first and second earpieces configured to extend along sides of the patient's face and over each of the patient's ears, and a bridge extending between the two earpieces and over the patient's nose bridge, the frame including at least one engagement member configured to releasably engage one of the at least one disposable treatment patch. Additionally or alternatively, the wearable device further comprises a return electrode coupled to the frame, and the device is configured to provide a monopolar therapy.

An illustrative and non-limiting example takes the form of a wearable device for providing therapy to a patient, the device comprising: a frame configured to be worn on the patient's face, the frame including a first and second earpiece configured to extend along each side of the patient's face and over the patient's ears, and a bridge extending between the two earpieces and over the patient's nose; a plurality of prongs extending from the frame, each prong having a contact configured to contact skin of the patient's face when the frame is in position on the patient's face; and a plurality of electrodes configured to provide therapy to the patient, one electrode disposed on each contact point.

Additionally or alternatively, at least some of the plurality of prongs are hinged and move between a first, contracted position in which the plurality of prongs are aligned with the frame, and a second, expanded position in which the plurality of prongs extend at an angle from the frame and into contact with the skin.

Additionally or alternatively, for several of the preceding examples having an earpiece, the wearable device may further comprise at least one earpiece electrode carried on at least one of the earpieces. Additionally or alternatively, for several preceding examples, at least on electrode is configured for placement on the upper eyelid of a patient. Additionally or alternatively, several preceding examples may further comprise a power source and a control circuit coupled to the power source, the control circuit configured to issue electrical signals using the electrodes on the first and second treatment pads.

Another illustrative and non-limiting example takes the form of a wearable device for providing therapy to a patient, the device comprising: first and second treatment pads each including an electrode configured to provide therapy to the patient's eyes; a frame configured to be worn on the patient's nose, the frame extending between and connecting the first and second treatment pads; and a first battery disposed within the first treatment pad and a second battery disposed within the second treatment pad. Additionally or alternatively, the first and second batteries are rechargeable, wherein the wearable device further comprises a charging unit configured to receive the first and second treatment pads to recharge the first and second batteries. Additionally or alternatively, the electrode within each of the first and second treatment pads comprises at least two electrodes to facilitate bipolar stimulus output.

Another illustrative and non-limiting example takes the form of a wearable device for providing therapy to a patient, the device comprising: a treatment patch configured to be attached to the patient's face; at least one electrode disposed on the treatment patch, each electrode configured to provide therapy to one of the patient's eyes; and a controller containing circuitry electrically coupled to the treatment patch, the controller configured to control electrical therapy delivered by the electrode. Additionally or alternatively the wearable device further comprises a return electrode configured to be attached to the patient's neck, shoulder, or chest.

Another illustrative and non-limiting example takes the form of a wearable device for providing therapy to a patient, the device comprising a frame having a front piece and first and second arms extending therefrom, the front piece including a nosepiece and carrying at least one front electrode or front electrode pad thereon, the first and second arms extending from the front piece to first and second earpieces, respectively, which are shaped to contact and rest, at least partly, on the ear of a user, at least one of the earpieces carrying an earpiece electrode, the device further a control circuit and a power source, the control circuit configured to issue electrical signals through the front electrode or front electrode pad and the earpiece electrode to provide therapy to the eye of a user.

Additionally or alternatively, the front electrode or front electrode pad is adjustably coupled to the front piece to be held against the forehead of the user. Additionally or alternatively, the front electrode or front electrode pad is adjustably coupled to the front piece to be held against an upper eyelid of the user. Additionally or alternatively, the front electrode or front electrode pad is coupled to the nosepiece. Additionally or alternatively, the wearable device may be characterized by the omission of any electrode on the face of the user below the palpebral aperture. Additionally or alternatively, the power source may be any of a single use, primary cell, rechargeable, or replaceable battery.

Additionally or alternatively, the control circuit is contained in the first earpiece, and the power source is contained in the second earpiece. Additionally or alternatively, at least one of the first and second earpieces are detachable. Additionally or alternatively, the front piece comprises a first expanded portion and a second expanded portion on either side of the nosepiece, the control circuit being contained in the first expanded portion and the power source being contained in the second expanded portion. Additionally or alternatively, the control circuit is contained in the nose piece. Additionally or alternatively, the power source is contained in the nose piece. Additionally or alternatively, the first and second earpieces are shaped to at least partly wrap around the ears of the user. Additionally or alternatively, the earpiece electrode is held on a flexible or moveable arm. Additionally or alternatively, the front piece is configured to receive first and second lenses. Additionally or alternatively, the wearable device may further comprise an on/off switch actuatable by a user and carried on one of the first and second earpieces.

Another illustrative and non-limiting example takes the form of a wearable device for providing therapy to a patient, the device comprising: first and second treatment pads each including an electrode configured to provide therapy to the patient's eyes; a frame configured to be worn on the patient's nose, the frame extending between and connecting the first and second treatment pads; and a first battery disposed within the first treatment pad and a second battery disposed within the second treatment pad. Additionally or alternatively, the first and second batteries are rechargeable, wherein the wearable device further comprises a charging unit configured to receive the first and second treatment pads to recharge the first and second batteries.

Another illustrative and non-limiting example takes the form of a wearable device for providing therapy to a patient, the device comprising: a frame configured to be worn on the patient's face, the frame including a first and second earpiece configured to extend along each side of the patient's face and over the patient's ears, and a bridge extending between the two earpieces and over the patient's nose; a plurality of prongs extending from the frame, each prong having a contact configured to contact skin of the patient's face when the frame is in position on the patient's face; and a plurality of electrodes configured to provide therapy to the patient, one electrode disposed on each contact point.

An illustrative and non-limiting method example may comprise the steps of a user donning any of the preceding wearable devices, or alternatives thereto, to place the one or more electrodes thereof at a desired, instructed, or therapeutic position, and activating circuitry of the wearable devices, when so provided, to deliver therapy. Still another illustrative and non-limiting example comprises any of the preceding wearable devices issuing therapy pulses via the electrodes thereof for purposes of treating, reversing, preventing, arresting, or otherwise addressing a disease of the eye or surrounding tissues.

BRIEF DESCRIPTION OF THE DRAWINGS

The disclosure may be more completely understood in consideration of the following detailed description of various embodiments in connection with the accompanying drawings, in which:

FIG. 1A shows a person wearing an illustrative medical device;

FIG. 11B shows details of the medical device of FIG. 11A;

FIGS. 14A-14F illustrate another illustrative medical device;

FIGS. 15A-15B show another illustrative medical device;

FIGS. 17A-17D show another illustrative medical device.

Figure 1B:
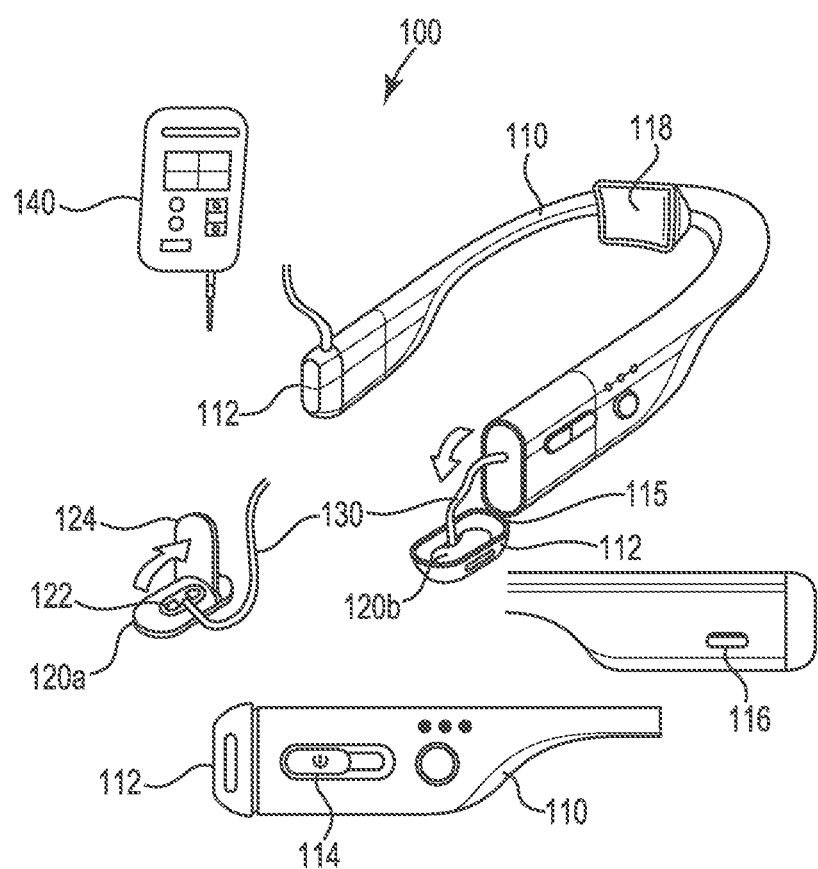
FIG. 1B shows various components of the medical device of FIG. 1A

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5). Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "withdraw", variants thereof, and the like, may be generally considered with respect to the positioning, direction, and/or operation of various elements relative to a user/operator/manipulator of the device, wherein "proximal" and "withdraw" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete elements together.

It is noted that references in the specification to "an embodiment", "an example", "some embodiments", "some examples", "other embodiments", "other examples", etc., indicate that the embodiment(s) or example(s) described may include a particular feature, structure, or characteristic, but every embodiment/example may not necessarily include the particular feature, structure, or characteristic. Moreover, such phrases are not necessarily referring to the same embodiment/example. Further, when a particular feature, structure, or characteristic is described in connection with an embodiment/example, it would be within the knowledge of one skilled in the art to effect the particular feature, structure, or characteristic in connection with other embodiments/examples, whether or not explicitly described, unless clearly stated to the contrary. That is, the various individual elements described below, even if not explicitly shown in a particular combination, are nevertheless contemplated as being combinable or arrangeable with each other to form other additional embodiments/examples or to complement and/or enrich the described embodiment(s)/example(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments/examples, alterations of and deviations from previously-used to numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The following description should be read with reference to the drawings, which are not necessarily to scale, wherein similar elements in different drawings are numbered the same. The detailed description and drawings are intended to illustrate but not limit the disclosure. Those skilled in the art will recognize that the various elements described and/or shown may be arranged in various combinations and configurations without departing from the scope of the disclosure. The detailed description and drawings illustrate example embodiments/examples of the disclosure. However, in the interest of clarity and ease of understanding, while every feature and/or element may not be shown in each drawing, the feature(s) and/or element(s) may be understood to be present regardless, unless otherwise specified.

Dry macular degeneration is an eye disorder typically affecting people over 50 years old. It may progress to wet macular degeneration when blood vessels grow under the retina and leak. Although rare, macular degeneration does occur in children and teenagers. Stargardt's disease is one form of macular degeneration found in younger people. Conventional treatment for early dry macular degeneration is through nutritional and supplement therapy. Wet macular degeneration may be treated with laser photocoagulation and drug therapy, although these treatments have major limitations. Alternative treatments and devices are needed.

Embodiments of wearable devices that may be used for providing therapy include electrical current, ultrasound, light, transcutaneous or percutaneous infusion or injection devices, magnetic therapy devices, etc. The invention is directed to the various features that can be provided for a wearable device. For conciseness the disclosure will discuss embodiments for providing electrotherapy to the eye via electrodes applied above or around the eye, however it should be understood that alternative forms of energy may be provided by the devices and systems disclosed herein. In addition, while many embodiments will be discussed in terms of energy delivery it is understood that the electrodes, devices and systems also can provide for receiving information from the body and data collection. The wearable devices may be useful for the treatment and/or diagnosis of a variety of ophthalmic conditions such as cataracts, diabetic retinopathy, macular degeneration, refractive errors, glaucoma, corneal conditions including corneal lesions and abrasions including surgical wounds, inherited retinal disease, presbyopia, retinitis pigmentosa, Stargardt's, CMV-retinitis, Best's disease, macular dystrophy, optic neuritis, ischemic anterior optic neuritis, Usher's syndrome, Leber's congenital amaurosis, cone-rod dystrophy, cone dystrophy, choroideremia, gyrate atrophy, central retinal artery occlusion, central retinal vein occlusion, branch retinal artery occlusion, branch retinal vein occlusion, central serous chorioretinopathy, conditions amenable to nerve stimulation, including but not limited stimulating the facial nerve, such as dry eye, cystoid macular edema, ocular histoplasmosis, ocular toxoplasmosis, retinopathy of prematurity, amblyopia, strabismus, nystagmus, and any other ophthalmic, eye, or vision-related condition. In alternative embodiments, the systems disclosed herein may also be used to optimize or improve vision for eyes that are "normal" or have not pathology.

A variety of electrical parameters for electrical output therapy are disclosed herein. It should be understood that the apparatuses disclosed may be used to deliver electrical therapy outputs having other parameters than those specifically disclosed (such as at different frequency, wave shape, amplitude, pulse width, etc.). Such therapy can be current controlled or voltage controlled, all within the scope of the present invention.

As will be described in greater detail below, FIG. 1A illustrates an example of a wearable device 100 which may be utilized to provide therapy, such as electrotherapy to the eyes of a patient. Specifically, FIG. 1A illustrates the wearable device 100 having a housing 110 and a pair of treatment pads 120a, 120b each attached to the housing 110 by a connector 130. The housing 110 may be configured to extend at least partially around the patient's neck. As shown in FIG. 1A, the housing 110 may be U-shaped to surround the neck. For example, the housing 110 may extend from one collarbone around the back of the neck and to the opposite collarbone.

The housing 110 may include at least one compartment configured to receive the treatment pads 120a, 120b when not in use. As shown in FIG. 1B, in some examples, the compartment may include end caps 112 disposed on the free ends of the U-shaped housing 110. Each end cap 112 may have a recess configured to hold one of the treatment pads 120a, 120b. The end caps 112 may have a hinge connection 115 to the housing 110, as shown in FIG. 1B. In other examples, the end caps 112 may have a friction fit or snap fit with the housing 110. In some examples, the connector 130 may be retractable within the housing 110 when the treatment pads 120a, 120b are disposed in the end caps 112. When the end caps 112 are opened, the treatment pads 120a, 120b may be pulled out, extending the connector 130 so the treatment pads 120a, 120b reach the eyes when the housing 110 is in place around the neck, as shown in FIG. 1A. In some examples, the treatment pads 120a, 120b may retract against or into the end of the housing 110. In some examples, the treatment pads may be absent and the user may instead use a set of goggles or a glasses-type frame that carries therapy electrodes thereon.

The housing 110 may include a return electrode 118 configured to contact skin on a portion of the patient's body spaced apart from the eye region. As shown in FIG. 1B, the return electrode 118 may be positioned on an inner surface of the base of the U-shaped housing 110 such that it contacts the back of the patient's neck when the housing 110 is worn by the patient as illustrated in FIG. 1A. However, it should be understood that the return electrode 118 may be placed on any portion of the patient's body spaced apart from the eye area, including the temple, on or behind the ear, mouth, neck, shoulder, chest, back of the hand, arm, etc.

Each treatment pad 120a, 120b may include at least one electrode 122 configured to provide therapy to an eye region of the patient. The connector 130 may electrically connect the electrode 122 on each treatment pad 120a, 120b to circuitry inside the housing 110. The treatment pads 120a, 120b may each include a treatment patch 124 disposed over the electrode 122. In some examples, the treatment pads 120a, 120b may include a permanent treatment patch 124 that is reusable and defines a cleanable surface. In other examples, the treatment pads 120a, 120b may include a removable, disposable treatment patch 124. The treatment patch 124 may include a biocompatible adhesive configured to adhere the treatment pads 120a, 120b to the patient's skin. In some examples, the treatment patch 124 may include adhesive on both sides, the first side to adhere to the electrode 122 and treatment pad 120a, 120b, and the second side to adhere to the patient's skin. A plurality of disposable treatment patches 124 may be provided, for example, in the end caps 112, another region of the housing 110, or in a separate container. The treatment patch 124 may include a window for allowing electrode 122 to contact tissue. In other examples, the treatment patch 124 itself may define the electrode 122. For example, the treatment patch 124 may be conductive in nature, such as by using a conductive hydrogel or conductive adhesive to both hold the treatment patch 124 on user tissue and to conduct current therethrough. In some examples, the electrode 122 may be attached to a surface of the treatment patch 124 or be embedded within the treatment patch 124. In some examples, the treatment patch 124 may be made of a gel or padded material to provide a cushioned surface against the skin.

The housing 110 contains electronics for providing a therapy output. For example, a microcontroller, state machine, discrete logic, one or more application specific integrated circuits (ASICs), various discrete components (resistors, diodes, switches, transistors, capacitors, inductors), amplifiers, etc. may be provided as the electronics of the system. In an example, the electronics may include a microcontroller coupled to communication circuitry (such as Bluetooth or other RF wireless, inductive, or optical circuitry) to receive control signals, programming information, and to provide diagnostic and device history data. The microcontroller may be coupled memory elements, such as a flash memory chip or the like, or other suitable volatile or non-volatile memory, to store program instructions, therapy parameters, diagnostic and history information. The microcontroller may be coupled to and control the operation of sensing circuitry (such as a buffer, sampling, amplifier, filter, and analog-to-digital conversion circuitry) as well as output circuitry which may include a voltage source, a current source, a transducer (for example to provide an ultrasound or other mechanical output as well as to control a pump or infusion apparatus that delivers a chemical or biological substance), and/or light generating circuitry (such as a VCSEL, LED, laser diode, or other circuit or component that converts electricity to light. The microcontroller may be replaced by a microprocessor or by a state machine, if desired.

In some examples, the housing 110 may include at least one rechargeable battery configured to power the pulse generator or control circuitry, which in turn provides therapeutic signals to the electrode 122 on each treatment pad 120a, 120b. A charging port 116 such as a USB charging port may be provided on the housing 110 to allow for recharging the battery. In some examples, rather than a rechargeable battery, a replaceable battery may be provided, both in the embodiment of FIG. 1 as well as in any of the other examples that follow.

The housing 110 may also include an on/off switch 114 to activate the electrodes 122. In some examples, a separate control unit 140 may be used with the wearable device 100. The control unit 140 may have a wired or wireless (cellular phone, Bluetooth, etc.) connection to the housing 110 and may be used by the physician to set and/or modify treatment parameters for the electrodes 122.

In use, the patient places the housing 110 around his or her neck with the return electrode 118 in contact with the skin on the back of the neck. The end caps 112 are opened and the treatment pads 120a, 120b are removed and the connectors 130 extended. In some examples, a new treatment patch 124 may be disposed over the electrode 122 and the treatment patch 124 placed over the eyelid, as shown in FIG. 1A. The two treatment pads 120a, 120b may be used together to treat both eyes simultaneously, or a single treatment pad 120 may be used to treat only one eye, while the other treatment pad 120 remains in the end cap 112 of the housing 110. The on/off switch 114 is moved to the "on" position and the electrode 122 delivers therapy to one or both eyes. Alternatively, the "on" position may put the system into an active mode that is activated to deliver energy by a separate command from a remote control or other activation system. Prior to delivering energy the system may include a pre-check that confirms appropriate impedance prior to therapy delivery.

The parameters of the therapy may be dictated by a physician through the control unit 140. The control unit may alternatively or in addition be operated by the patient to deliver pre-determined therapy parameters that have been programmed by the physician on the control unit 140 or from a remote programmer not pictured. The physician may program the treatment parameters during an office visit. Treatment may be fixed by the physician, or may be modifiable by the patient within parameters set by the physician. Once the treatment session is complete, the patient removes the treatment pads 120 from the eyes, removes and disposes of the treatment patches 124, and returns the treatment pads 120 to the end caps 112 for storage. The batteries within the housing may be recharged by plugging a USB charging cord into the charging port 116. In addition or in the alternative, the batteries may be replaceable. In examples with a permanent treatment patch 124, it may be cleaned after each use with a disinfectant and/or wetted such as by adding a saline solution or hydrogel before each use to aid in conducting current to and through user tissue.

Therapy may be provided in a monopolar fashion, with current flowing between the electrodes 122 and the return electrode 118, or in bipolar fashion, with current flowing between two of electrodes 122. In another example, the electrodes 122 may include two or more discrete contacts each, that is, in the form of a compound electrode having a plurality of separately addressable electrical nodes in close proximity to one another.

A variety of examples of electrical subsystems that may be implemented in addition to or in place of that just discussed may be found in any of U.S. Pat. No. 7,251,528 and/or U.S. patent application Ser. No. 16/589,383 (published as US PG Pub. No. 20200101290), Ser. Nos. 16/697,689, and 16/844,421, and/or U.S. Provisional Patent Applications 62/867,421, and/or 62/873,450, the disclosures of which are incorporated herein by reference.

Figure 2:
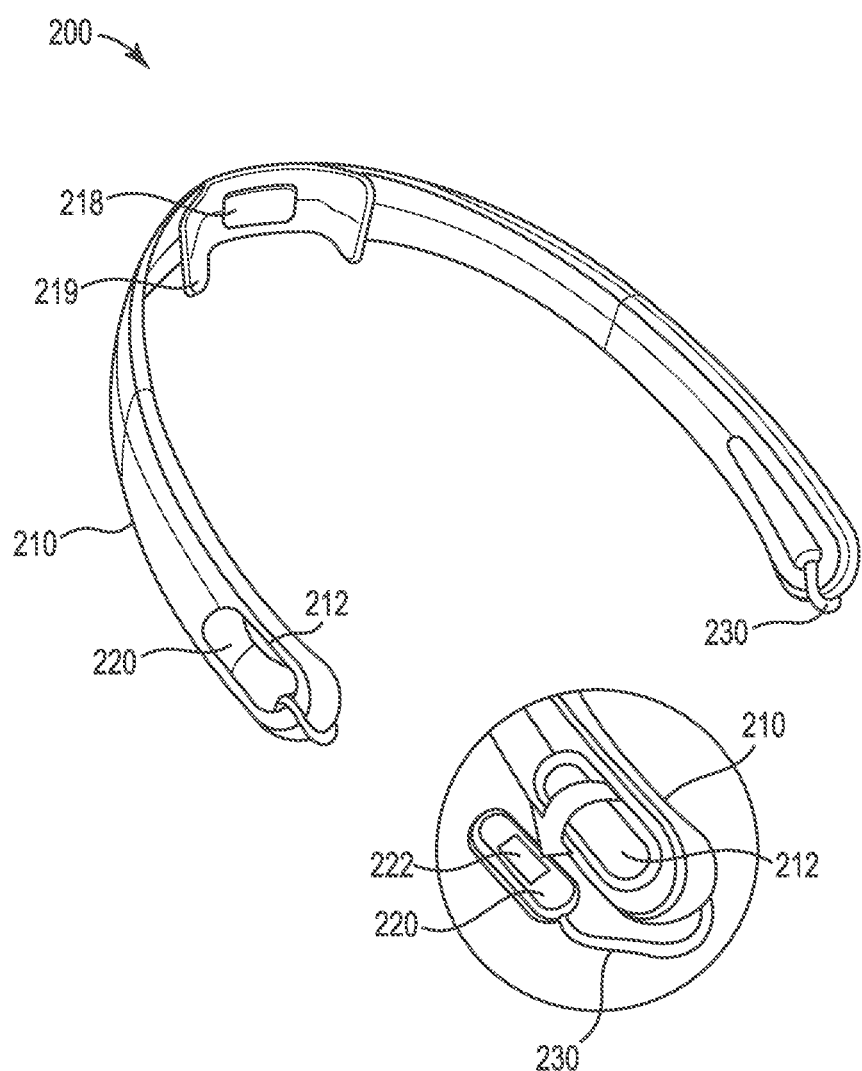
FIG. 2 shows another illustrative medical device.

FIG. 2 shows another wearable device 200 including a housing 210 and treatment pads 220 connected to the housing 210 by connectors 230. The housing 210 as shown includes an adhesive pad 219 surrounding the return electrode 218 to aid in keeping the return electrode 218 in contact with the skin when the housing 210 is disposed around the patient's neck. In the example shown in FIG. 2, the housing includes recesses 212 adjacent the free ends of the U-shaped housing 210. The recesses 212 may be configured to receive the treatment pads 220 when not in use. The connectors 230 may be retractable within the housing 210 when the treatment pads 220 are disposed within the recesses 212. The treatment pads 220 may be received within the recesses 212 by a snap fit or friction fit, with the electrodes 222 facing the housing 210 to protect the electrodes 222. As with the example shown in FIG. 1B, the treatment pads 220 may have a permanent treatment surface or may be used with removable and disposable treatment patches as described above. The wearable device 200 may be used as described above with regard to wearable device 100. The housing 210 may contain electronics and a power source similar to those described above relative to housing 110.

Figure 3A:
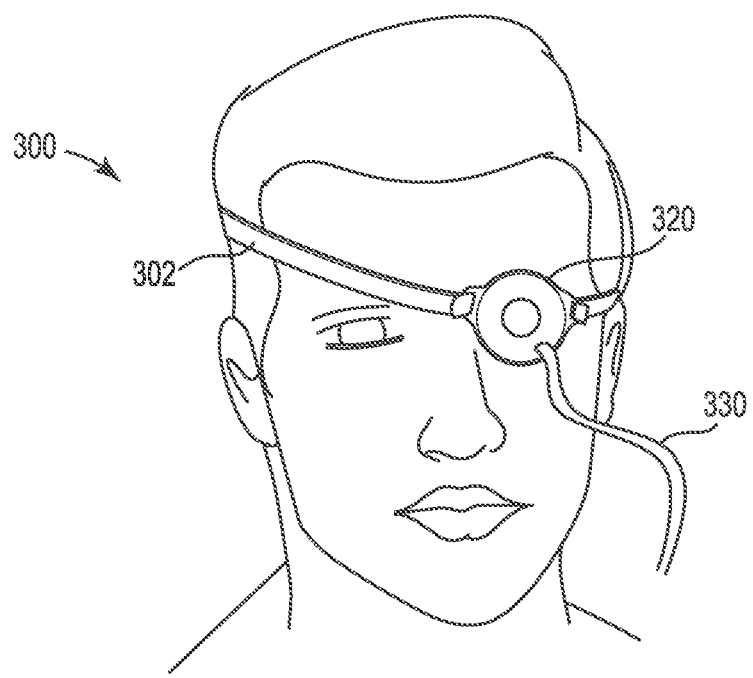
FIG. 3A shows a person wearing another illustrative medical device.
Figure 3B:
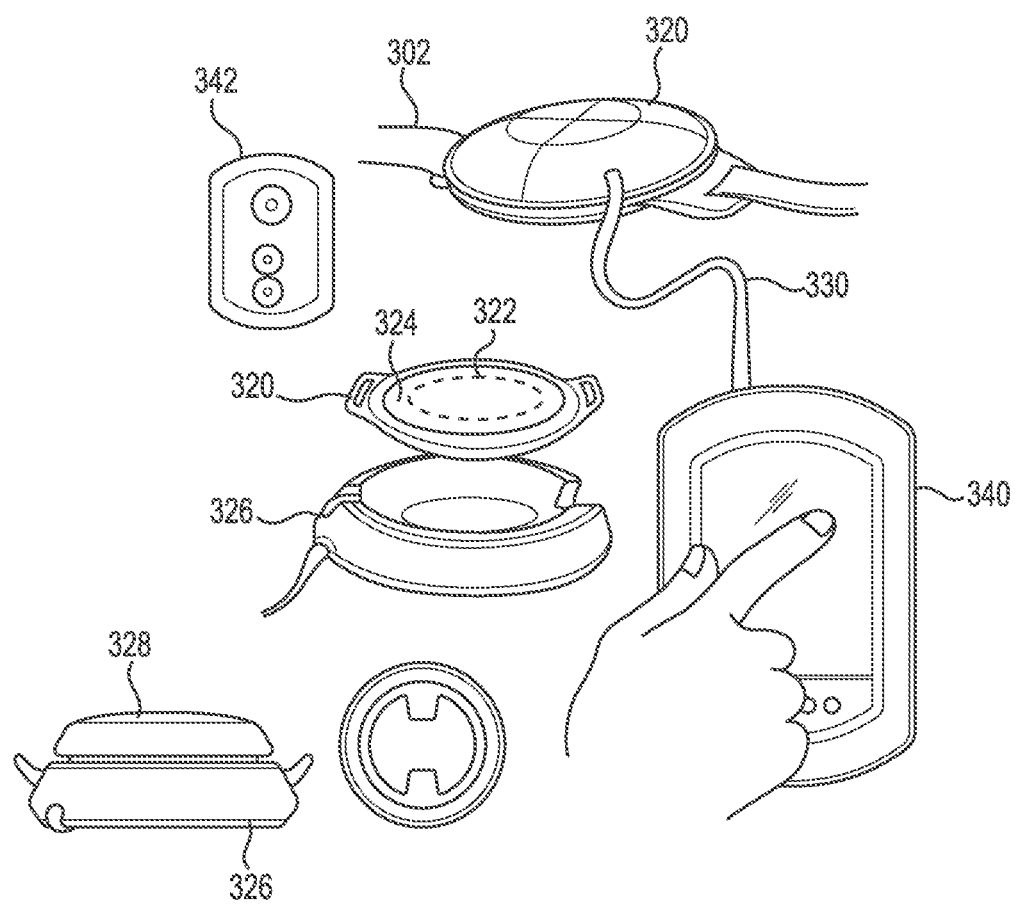
FIG. 3B shows various components of the medical device of FIG. 3A.

FIG. 3A illustrates another example of a wearable device 300 for providing therapy to a patient. The wearable device 300 may include a treatment pad 320 with an adjustable head strap 302 and a connector 330 connectable to a controller 340 (shown in FIG. 3B) containing circuitry electrically connected to the treatment pad 320. The controller 340 may contain electronics similar to those described above relative to housing 110. In some examples, the treatment pad 320 may instead contain the electronics, and the controller 340 may be omitted and/or the connector 330 tethering the controller 340 to the treatment pad 320 may be omitted, such that the controller 340 serves as a wireless remote control.

The wearable device 300 may have a single treatment pad 320 and be used to treat only one closed eye at a time, as shown in FIG. 3A. This wearable device 300 may allow the patient to keep the uncovered eye open. The treatment pad 320 may include an electrode 322 configured to provide therapy to an eye of a patient. More than one electrode 322, such as having at least two separately addressable electrodes, may be provided on a device 300. A treatment patch 324 may be disposed over the electrode 322, similar to the treatment pad 120 described above. In some examples, the treatment patch 324 may be a gel patch. The treatment patch 324 may be permanent, and may be disinfected after each use, or wetted prior to use such as by adding a saline or hydrogel thereto, or the treatment patch 324 may be removable and disposable. A disposable treatment patch 324 may be attached to the treatment pad 320 with adhesive.

The treatment pad 320 may also include a rechargeable battery (not shown) and may be charged by placing the treatment pad 320 on a charging unit 326. The charging unit 326 may be an induction charging unit 326 plugged into a standard wall outlet and may include a lid 328 to protect the treatment patch 324 during charging. In some examples, the controller 340 may include a touch pad for programming and monitoring the treatment pad 320. In addition to or alternative to the controller 340, a remote control device 342 may be used to operate the treatment pad 120. The remote control device 342 may be wireless, operating on a cellular signal, Bluetooth, or other wireless control signal.

Figure 4:
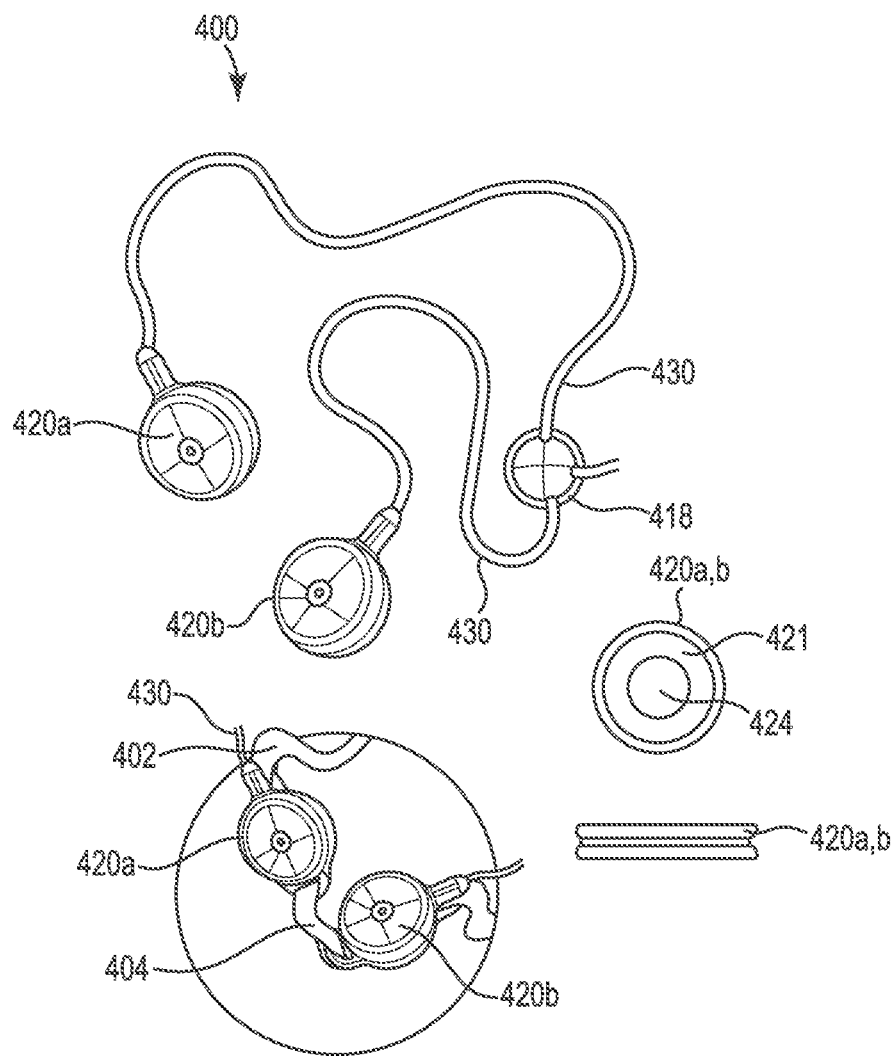
FIG. 4 shows various components of another illustrative medical device.

In another example, shown in FIG. 4, the wearable device 400 includes first and second treatment pads 420a, 420b, each having a connector 430 connecting the treatment pads 420 to a return electrode 418. One or both of the treatment pads 420a, 420b may contain electronics similar to those described above relative to housing 110. In one example, a rechargeable battery may be contained on one of the treatment pads 420a, and electrically coupled to the other of the treatment pads 420b which houses the electronics for the system, thereby distributing the weight of the battery and electronics across the two pads 420a, 420b.

The return electrode 418 may be configured to be placed on the any portion of the patient's body spaced apart from the eye area, including the temple, on or behind the ear, mouth, neck, back, shoulder, chest, back of the hand, arm, etc. Each of the first and second treatment pads 420a, 420b may include a treatment patch 424 for contacting the patient's eyelid. The treatment patch 424 may be a gel patch. In some examples, the treatment pads 420a, 420b and the return electrode 418 may have an adhesive backing 421 for attaching the treatment pad 420a, 420b to the eyelid. Each treatment pad 420a, 420b may include an electrode (not shown) configured to provide therapy to the eye. The electrodes may be disposed under the treatment patch 424, as described above with regard to treatment pads 120a, 120b and shown in FIG. 1B.

The wearable device 400 may have a head strap 402 connecting the two treatment pads 420a, 420b around the back of the head, and a strap 404 extending between the eyes to provide eye to eye axis adjustability. Both straps 402 and 404 can be a fixed size or be adjustable. The wearable device 400 may include a controller, charging unit, and remote control device as described above for the wearable device 300.

Figure 5:
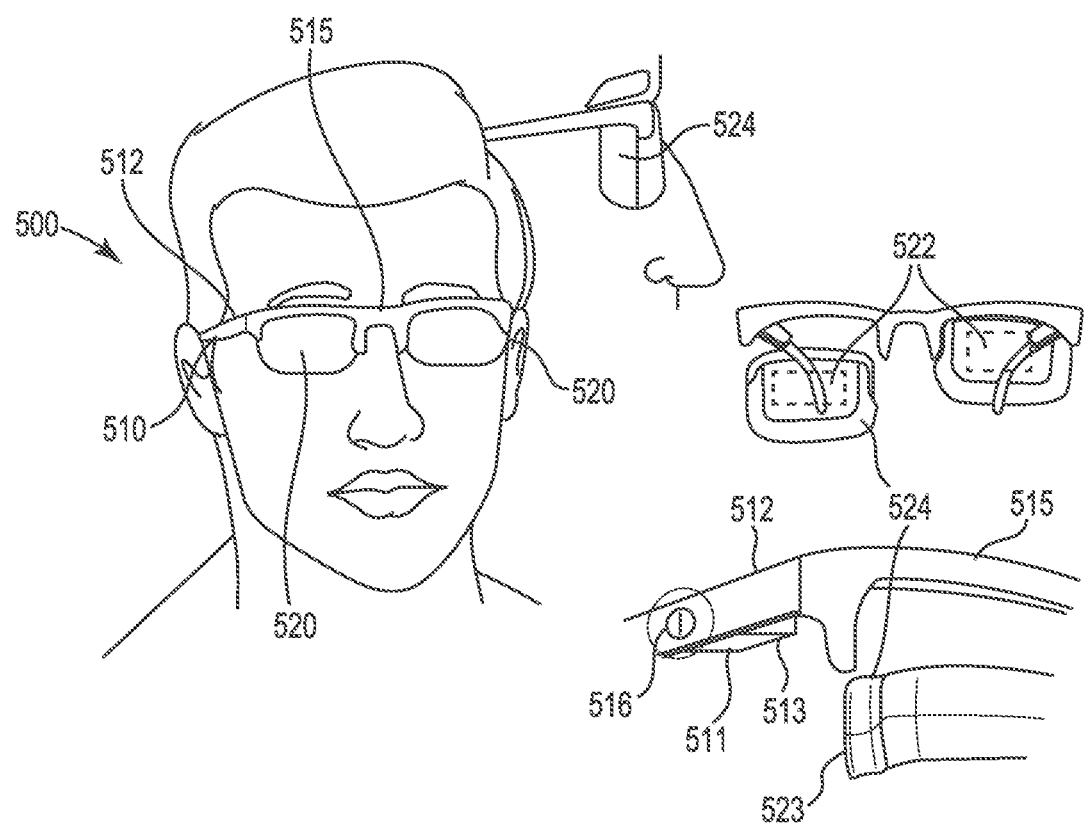
FIG. 5 shows various components of another illustrative medical device.

A wearable device 500 for providing therapy that looks similar to a pair of eyeglasses is shown in FIG. 5. The wearable device 500 may include first and second treatment pads 520 configured to provide therapy to the patient's eyes, and a frame 510 configured to be worn on the patient's face as eyeglasses. The frame 510 may include two earpieces 512 configured to extend along the sides of the face and over the ears, and a bridge 515 extending between the earpieces 512 and over the bridge of the nose. The treatment pads 520 may include treatment patches 524 configured to contact the closed eyelids. In some examples, the treatment patches 524 may be padded or may be gel pads. Each treatment pad 520 may include an electrode 522 disposed under the treatment patch 524, configured to provide therapy to the eye.

In order to provide adjustability so the treatment patches 524 are in contact with the eyelids when the wearable device 500 is placed on the patient with the earpieces 512 over the ears and the bridge 515 on the bridge of the nose, each earpiece 512 may include an adjustment member 511. The adjustment member 511 may be configured to move the treatment pad 520 toward and away from the eyelid relative to the frame 510, particularly the bridge 515. The adjustment member 511 may include an engagement member 513 configured to engage one of the treatment pads 520. In some examples, the engagement members 513 may engage the treatment pads 520 in a snap fit. As shown in FIG. 5, treatment pads 520 may each have a snap fit region 523 on an outer edge that is configured to couple to the engagement members 513 with a snap fit. The treatment pads 520 may be moved towards or away from the eyes, for example, by turning a screw 516, thereby adjusting the position of the treatment pad 520 to move it toward or away from the patient's face. The adjustability of the position of the treatment pads 520 allows the control of the desired level of contact with the eyelids, ensuring adequate electrical stimulation of underlying tissue from the electrode within the treatment pad 520, without undue pressure being applied to the eyes. In some embodiments, the system may be configured to run an impedance check and an indicator (for example, sound or light) may be provided to indicate when the appropriate level of pressure is being applied to provide a desired level of impedance for the energy delivered.

The frame 510 may contain electronics similar to those described above relative to housing 110. The wearable device 500 may include a rechargeable battery disposed within the frame 510. A charging port (not shown) similar to charging port 116 shown in FIG. 1B may be disposed on the frame 510, for example on one of the earpieces 512, to recharge the battery. In some examples, a return electrode (not shown) may be provided as a contact point on the frame 510, such as on one or both of the earpieces 512, and located to contact the patient behind the ear. In other examples, one or more return electrodes may be placed on any portion of the patient's body spaced apart from the eye area, including on the ear, temple, mouth, neck, back, shoulder, chest, back of the hand, arm, etc.

Figure 6:
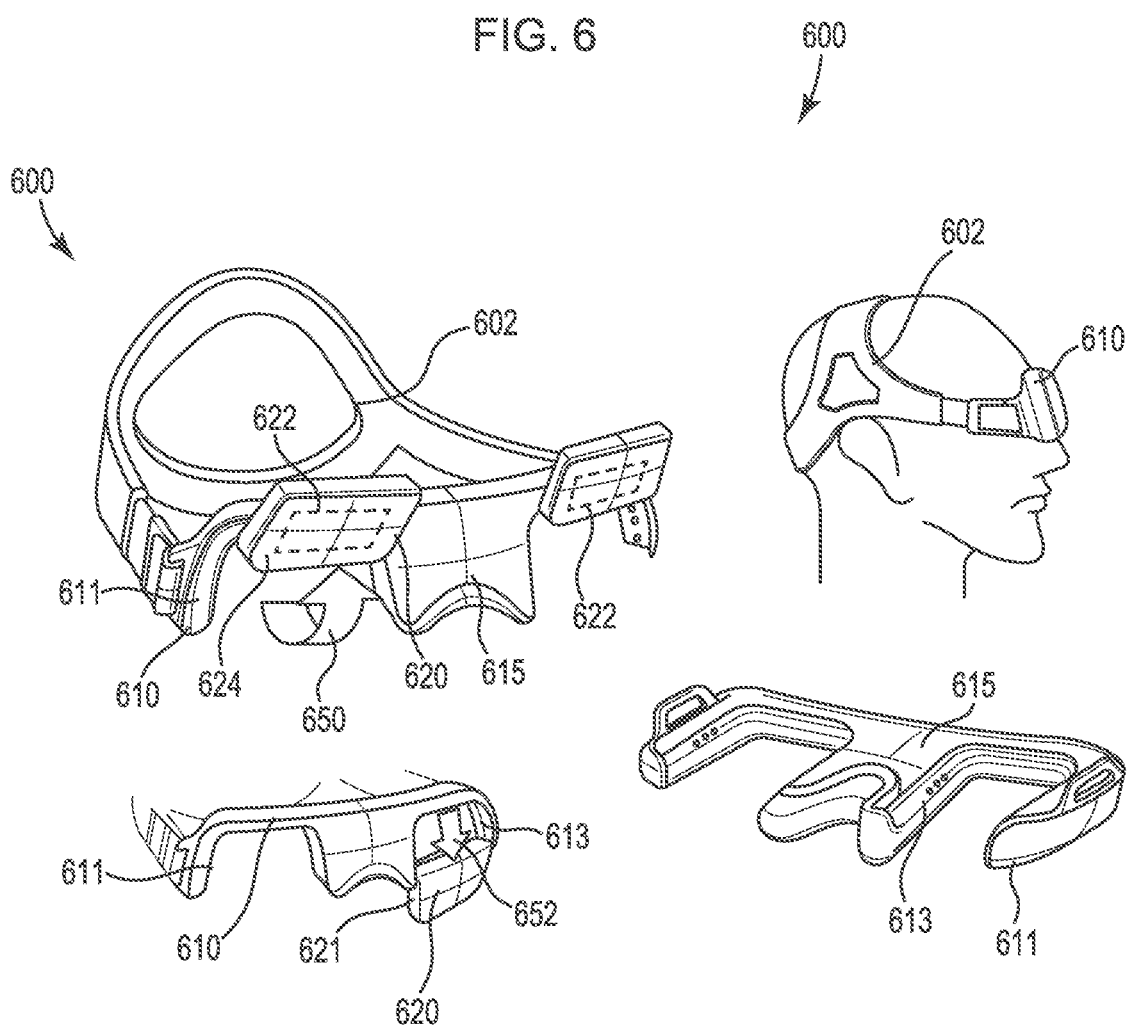
FIG. 6 shows various components of another illustrative medical device.

Another wearable device 600 for providing therapy that looks similar to a pair of eyeglasses or goggles is shown in FIG. 6. The wearable device 600 may include first and second treatment pads 620 configured to provide therapy to the patient's eyes, and a frame 610 configured to be worn on the patient's face as eyeglasses. The wearable treatment device 600 may include an adjustable head strap 602 coupled to the frame 610 and configured to secure the frame 610 to the patient's face with the first and second treatment pads 620 in contact with the patient's eyes. Alternatively, the adjustable head strap may be supplanted by an ear piece 512 shown in FIG. 5. The frame 610 may include a center bridge 615 between two pad-holding regions 611. The frame 610 may be configured to hold the first and second treatment pads 620 in a rotatable or sliding engagement. The rotatable engagement may be provided by a hinge disposed on the pad-holding region 611 and on the treatment pad 620, allowing the treatment pad 620 to be rotated up and away from the eyelid, as shown by arrow 650. The sliding engagement may be provided by a groove or channel 613 disposed on the inner surface of the pad-holding region 611 of the frame 610. The channel 613 may be configured to receive the edge 621 of the treatment pad 620 in a sliding friction fit. The treatment pad 620 may be removed from the frame 610 by sliding the treatment pad 620 downward, as shown by arrow 652.

The treatment pads 620 may include treatment patches 624 configured to contact the eyelids. In some examples, the treatment patches 624 may be padded or may be gel pads. Each treatment pad 620 may include an electrode 622 disposed under the treatment patch 624, configured to provide therapy to the eye. The treatment pads 620 may be removable and exchangeable, and the treatment patches 624 may be removable and disposable, or they may be permanently attached to the treatment pads 620. The treatment pads 620 may include multiple electrode contacts, for example located in a relative superior and position (i.e., one contacting the upper eyelid and one the lower, respectively) to provide bipolar energy delivery. In some examples, one or more return electrode (not shown) may be provided on the frame 610, head strap 602, or as a separate element electrically coupled to the device 600. The return electrode may be located to contact the patient on or behind the ear or on the temple. In other examples, one or more return electrodes may be placed on any portion of the patient's body spaced apart from the eye area, including on or near the mouth, neck, back, shoulder, chest, back of the hand, arm, etc.

The frame 610 may contain electronics similar to those described above relative to housing 110. The wearable device 600 may include a rechargeable battery disposed within the frame 610. A charging port (not shown) similar to charging port 116 shown in FIG. 1B may be disposed on the frame 610 to recharge the battery.

Figure 7A:
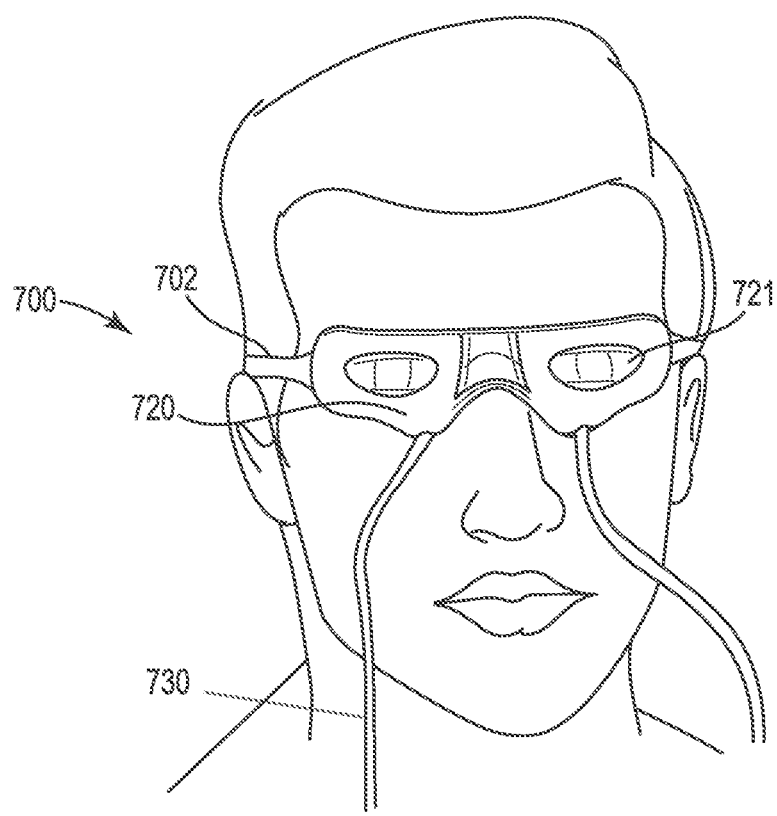
FIG. 7A shows a person wearing another illustrative medical device.
Figure 7B:
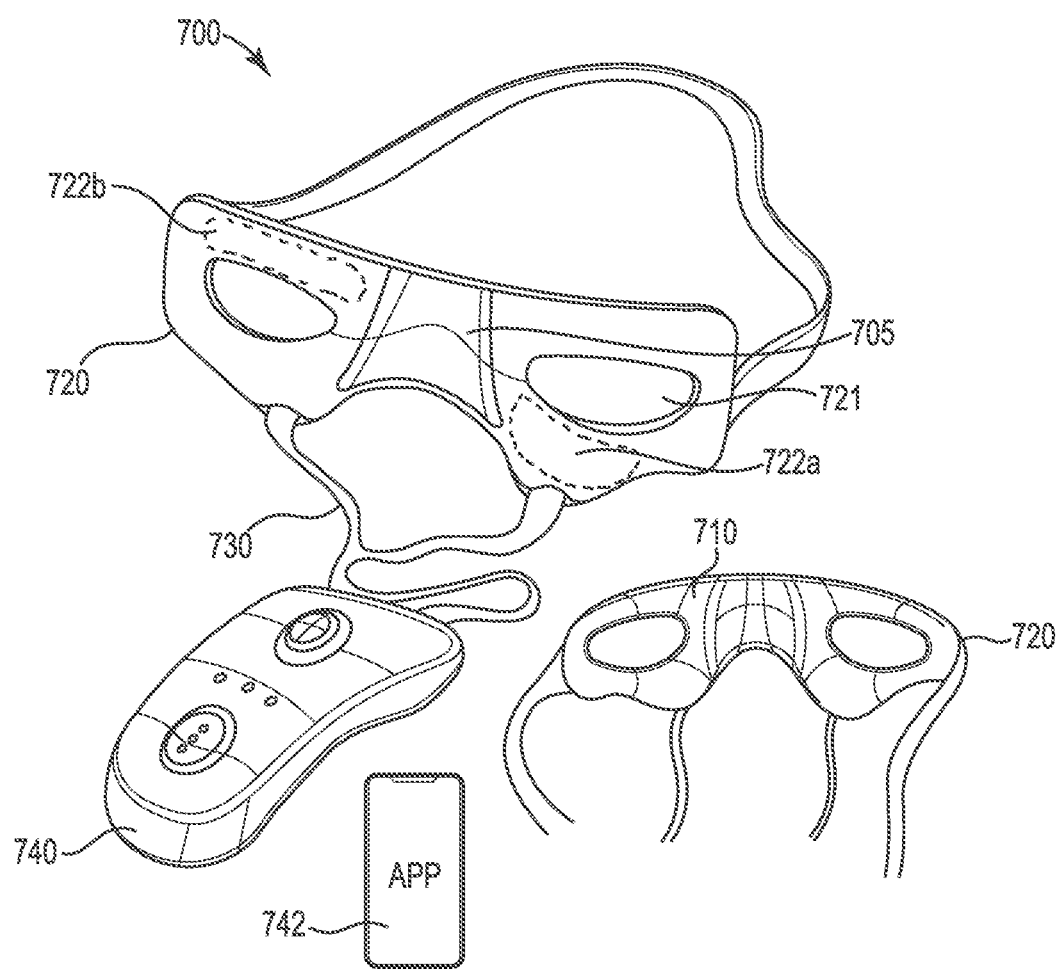
FIG. 7B shows various components of the medical device of FIG. 7A.

FIG. 7A illustrates another example of a wearable device 700 for providing therapy to a patient. The wearable device 700 may include a treatment mask 720 with an adjustable head strap 702 and a connector 730 connectable to a controller 740 (shown in FIG. 7B) containing circuitry electrically connected to the treatment mask 720. The treatment mask 720 may include first and second openings 721 for the patient's eyes, and may have a single electrode 722a adjacent one of the openings 721 to provide therapy to a single eye. In other examples, an electrode 722a, 722b may be disposed adjacent each of the first and second openings 721 to provide therapy to both eyes. The single electrode 722a may be positioned over the lower eyelid or over the upper eyelid (722b). When multiple electrodes 722a, 722b are present, they may both be positioned over the lower eyelid, over the upper eyelid, or one over the lower eyelid and one over the upper eyelid. The electrode 722a, 722b may be disposed on the surface of the treatment mask 720 or may be disposed within layers forming the treatment mask 720. In some examples, the electrode 722a, 722b may be used in a bipolar manner, such as by having more than one electrode adjacent each eye. In other examples, the electrode 722a, 722b may be used in a monopolar fashion, and a return electrode (not shown) may be disposed on the connector 730 and configured to be placed on any portion of the patient's body spaced apart from the eye area, including the temple, on or behind the ear, mouth, neck, back, shoulder, chest, back of the hand, arm, etc., as described above for return electrode 418 in FIG. 4.

The controller 740 may contain electronics similar to those described above relative to housing 110. The controller 740 may be configured to control electrical therapy delivery by the electrode 722. In some examples, the controller 740 may include a wall plug. In other examples, the controller 740 includes a battery, either a disposable battery or a rechargeable battery and a charging port. The controller 740 may allow the patient to turn the treatment mask 720 on and off. In some examples, the controller 740 may include wireless connectivity to a patient's or physician's cellular phone or tablet 742. The connectivity may be through a cellular signal, Bluetooth, or other wireless signal. In some examples, the mask 720 or headband 702 may instead carry the electronics, similar to those described above relative to housing 110.

The wearable device 700 may be used to treat the eyes while open, which may provide for an improved and more convenient experience for the patient. In some examples, the treatment mask 720 may include padded, foam, or gel regions. For example, the entire treatment mask 720 may include a foam, padded, or gel frame 710, to provide additional comfort to the patient. The treatment mask 720 may be formed from a flexible material such as fabric or polymer. In some examples, the treatment mask 720 may include a rigid or semi-rigid nose cover 705 configured to fit over the patient's nose. The nose cover 705 may aid in maintaining the flexible treatment mask 720 in the desired position on the patient's face. The nose cover 705 may be made of flexible metal or flexible polymer to provide a semi-rigid nose cover 705. As used herein "semi-rigid" encompasses materials having a rigidity greater than the material used to make the flexible treatment mask 720. In some examples, the nose cover 705 may be malleable, such that the patient may mold the nose cover 705 to their nose, providing a custom fit to the wearable device 700.

Figure 8A:
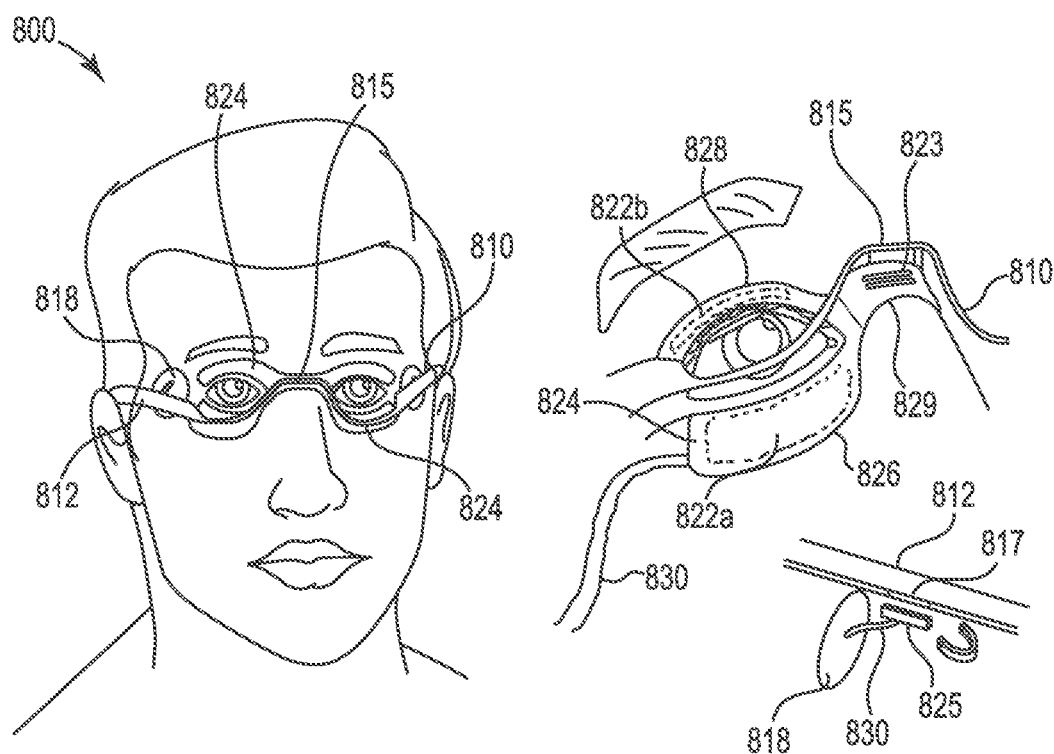
FIG. 8A shows a person wearing another illustrative medical device and details of that medical device.

Another example of a wearable device 800 for providing therapy is shown in FIG. 8A. The wearable device 800 may include at least one disposable treatment patch 824 configured to provide therapy to the patient's eyes, and a frame 810 configured to be worn on the patient's face as eyeglasses. The frame 810 may include two earpieces 812 configured to extend along the sides of the face and over the ears, and a bridge 815 extending between the earpieces 812 and over the bridge of the nose.

The treatment patch 824 may be configured to contact the skin around the eyes while the eyes are open. In some examples, the treatment patch 824 may include a lower region 826 configured to be placed on the skin below the eye and an upper region 828 configured to be placed on the upper eyelid. In some examples, each of the lower region 826 and upper region 828 may include a separate electrode 822a, 822b. In other examples, the entire treatment patch 824 may define a single electrode. The wearable device 800 may include an electrical connector 830 connecting the one or more electrode 822a, 822b to a controller (not shown). In some examples, the treatment patch 824 may include a first lower region 826 and first upper region 828 configured to surround a first eye, and a second lower region 826 and second upper region 828 configured to surround a second eye, with a bridge region 829 connecting the first and second lower regions 826 and first and second upper regions 828. The bridge region 829 may be configured to extend over the bridge of the nose. In some examples, the treatment patch 824 may be removably connected to the frame 810 with a snap fit, for example with a pad snap element 823 receiving a portion of the bridge 815 of the frame 810.

In some examples, the electrode 822a, 822b may be used in a monopolar manner, and the wearable device 800 may further include a return electrode 818 coupled to the earpiece 812 of the frame 810. In one example, the return electrode 818 may be provided as a contact point on the earpiece 812, and located to contact the patient behind the ear. In one example, the return electrode 818 may include an electrical connector 830 coupling the return electrode 818 to a first magnet 825 that may engage a second magnet 817 on the earpiece 812. The return electrode 818 may be coupled to the earpiece 812 such that the return electrode 818 may be placed on the patient's temple. In some embodiments, two return electrodes 818 may be provided, one on either earpiece 812. In other examples, the return electrode 818 may be placed on any portion of the patient's body spaced apart from the eye area, including on or behind the ear, mouth, neck, back, shoulder, chest, back of the hand, arm, etc. The frame 810 may contain electronics similar to those described above relative to housing 110.

Figure 8B:
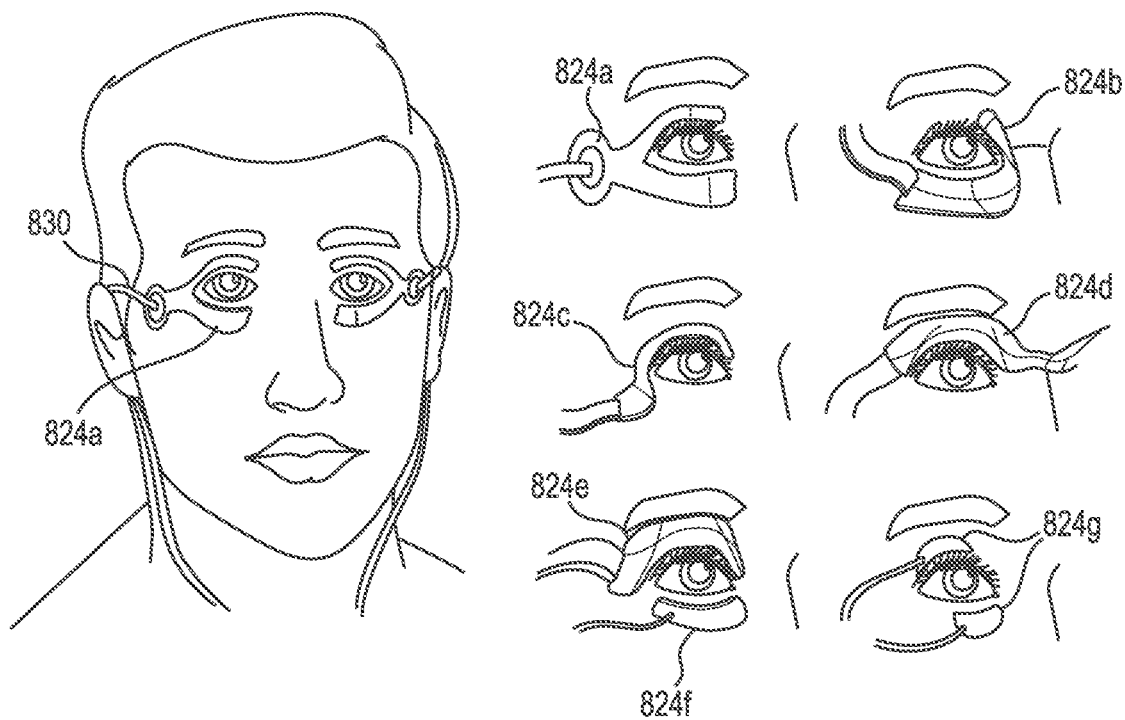
FIG. 8B shows various pad configurations for the medical device of FIG. 8A.

In some examples, the treatment patch 824 may be padded or may be gel pads. Each treatment patch 824 may be flexible and may have an adhesive backing to allow the patient to easily affix the treatment patch 824 onto the skin in the area to be treated, and to follow the contours of the face. In some examples, the treatment patch 824 may be made of fabric or a flexible polymer, and the electrode 822a, 822b may be disposed on the surface or embedded within the treatment patch 824. The treatment patches 824a-824g may be disposable and may have a variety of shapes and sizes, as shown in FIG. 8B. Regardless of the shape or size, each treatment patch 824a-824g may have an electrical connector 830 coupling the electrodes of the treatment patch 824a-824g to a controller. The treatment patches 824a-824g may be coupled to a portion of a frame 810, such as with a magnet, as discussed above with regard to the return electrode 818. In other examples, the treatment patches 824a-824g may be used without a frame, and simply adhered to the skin via the adhesive backing on the patch. The treatment patches 824a-824g may be used with a separate return electrode, or the electrode in the treatment patches 824a-824g may have two separate contacts for use in a bipolar fashion. In some examples a single treatment patch 824b, 824b, 824c, 824d may be used, while in other examples, two treatment patches 824e, 824f, 824g may be used. Various sizes and shapes of treatment patches 824a-824g may be used to customize the treatment area desired. Examples of areas where the treatment patches 824a-824g may be placed include, without limitation, the upper and lower eyelids, extending between the temporal (lateral) canthus and the nasal (medial) canthus. The treatment patches 824a-824g may extend across the upper eyelid crease and upper lid fold, lower eyelid crease, malar fold, infraorbital crease, nasojugal crease, and nasofacial sulcus.

Figure 9A:
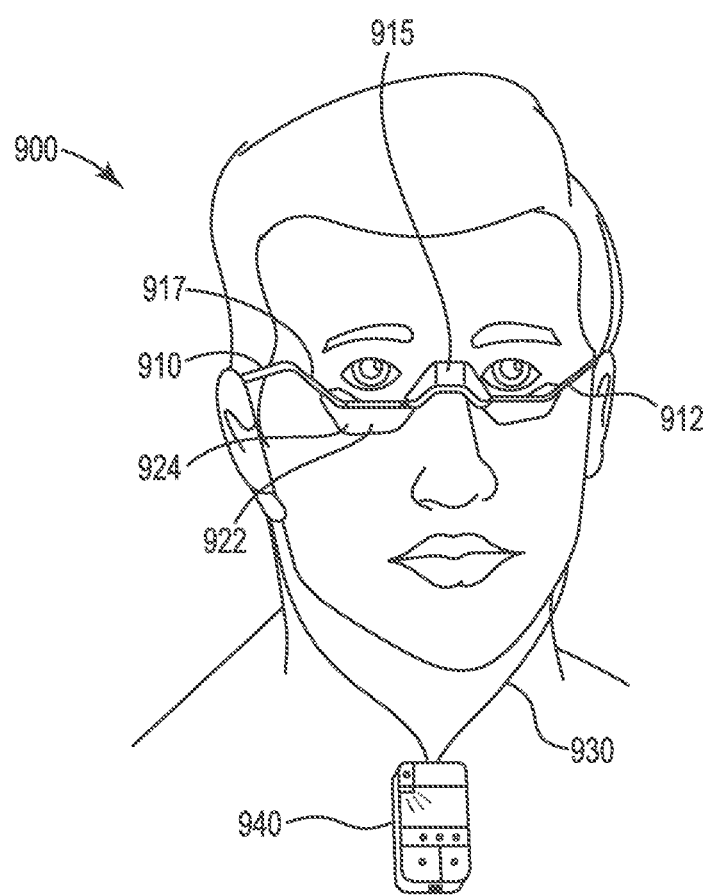
FIG. 9A shows a person wearing another illustrative medical device.
Figure 9B:
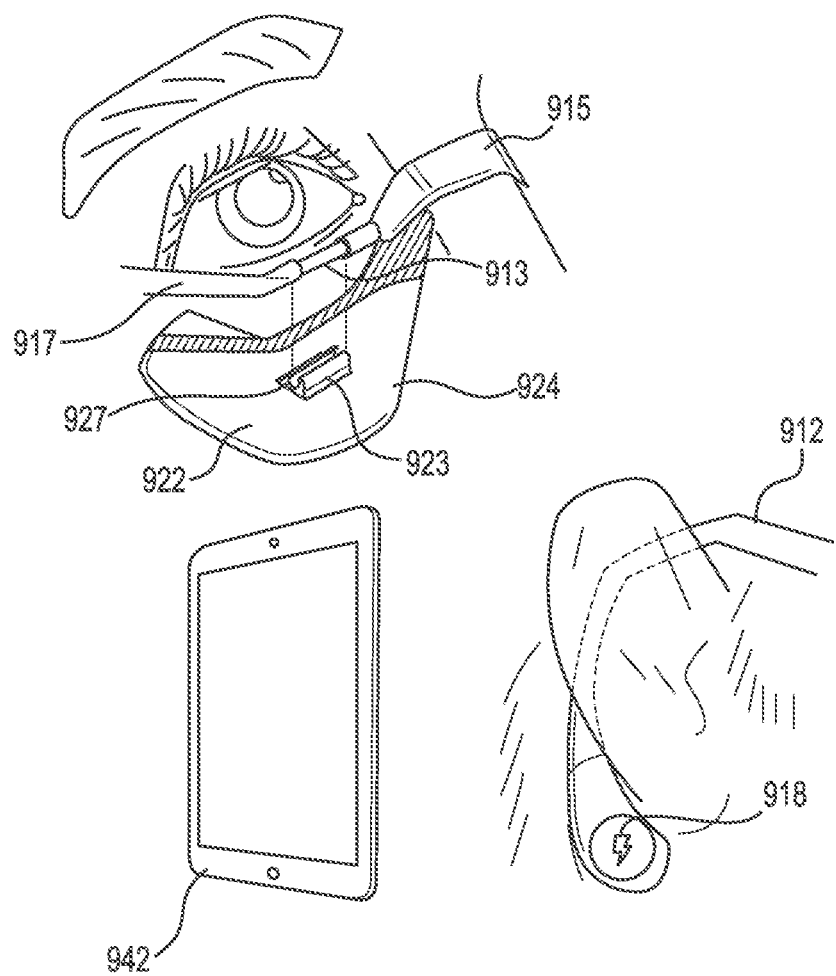
FIG. 9B shows details of the medical device of FIG. 9A.

FIGS. 9A and 9B illustrate another example wearable device 900 for providing therapy, particularly advantageous for therapy while the patient's eyes remain open. The wearable device 900 may include first and second treatment patches 924 configured to provide therapy to the patient's eyes, and a frame 910 configured to be worn on the patient's face as eyeglasses. The frame 910 may include two earpieces 912 configured to extend along the sides of the face and over the ears, lateral frame extensions 917 coupled to the treatment patches 924 and extending around the eyes, and a bridge 915 extending between the lateral frame extensions 917 and over the bridge of the nose. The treatment patches 924 may be configured to contact the skin below the eyes, as shown in FIGS. 9A and 9B, allowing the patient to more easily open his or her eyes during treatment. It will be appreciated that in the alternative the treatment patch 924 could alternatively or in addition be located above the eye by moving the lateral frame extension 917 above the eye.

The wearable device 900 may further include a controller 940 and electrical connectors 930 coupling electrodes 922 on the treatment patches 924 to electrical circuitry in the controller 940. The controller 940 may contain electronics similar to those described above relative to housing 110. Alternatively, the frame 910, for example, at the bridge 915 or earpieces 912 may instead have the electronics similar to those described above relative to housing 110.

In some examples, the treatment patch 924 may be disposable and may be removably connected to the frame 910 with a snap fit, for example with a snap element 923 on the treatment patch 924 including a channel 927 configured for receiving a tubular portion 913 of the lateral frame extension 917, as shown in FIG. 9B. Instead of traditional glasses type frames that are held off the face, the frame 910 may follow the contours of the face in order to hold the treatment patches 924 against the skin under the eyes.

In some examples, the entire treatment patch 924 may define an electrode 922. In other examples, a smaller electrode may be disposed on the surface of or embedded within the treatment patch 924. The treatment patch 924 and electrode 922 may be similar in material and configuration to treatment patch 824 and electrode 822a, 822b discussed above. In still further examples, the treatment patch 924 may be eliminated and the tubular portion 913 of the lateral frame extension 917 may include the electrode 922. The tubular portion 913 may be covered with a gel pad. The electrode 922 may be a used in a monopolar fashion, and the wearable device 900 may further include a return electrode 918 coupled to the earpiece 912. In one example, the return electrode 918 may be provided as a contact point on the earpiece 912, and located to contact the patient behind the ear, as shown in FIG. 9B. In some embodiments, two return electrodes 918 may be provided, one on either earpiece 912. In other examples, the return electrode 918 may be placed on any portion of the patient's body spaced apart from the eye area, including the temples, mouth, neck, back, shoulder, chest, back of the hand, arm, etc. Electrode 922 may also be used in a bipolar fashion by providing more than one electrical contact, such as by having two electrodes 922 that can be separately addressed (that is, separately used as anode and cathode, or as output and ground, or as current source and current sink).

In some examples, the controller 940 may communicate with a physician's unit 942 to receive programming information. The physician's unit 942 may monitor the treatment patch 924. The controller 940 may be wireless, operating on a cellular signal, Bluetooth, or other wireless control signal to receive and transmit information to the physician's unit 942.

Figure 10A:
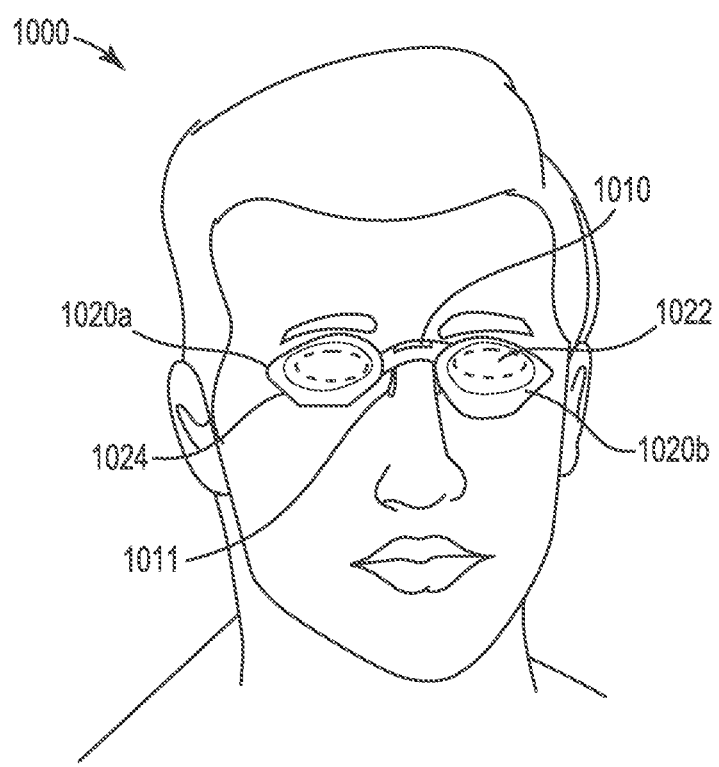
FIG. 10A shows a person wearing another illustrative medical device.
Figure 10B:
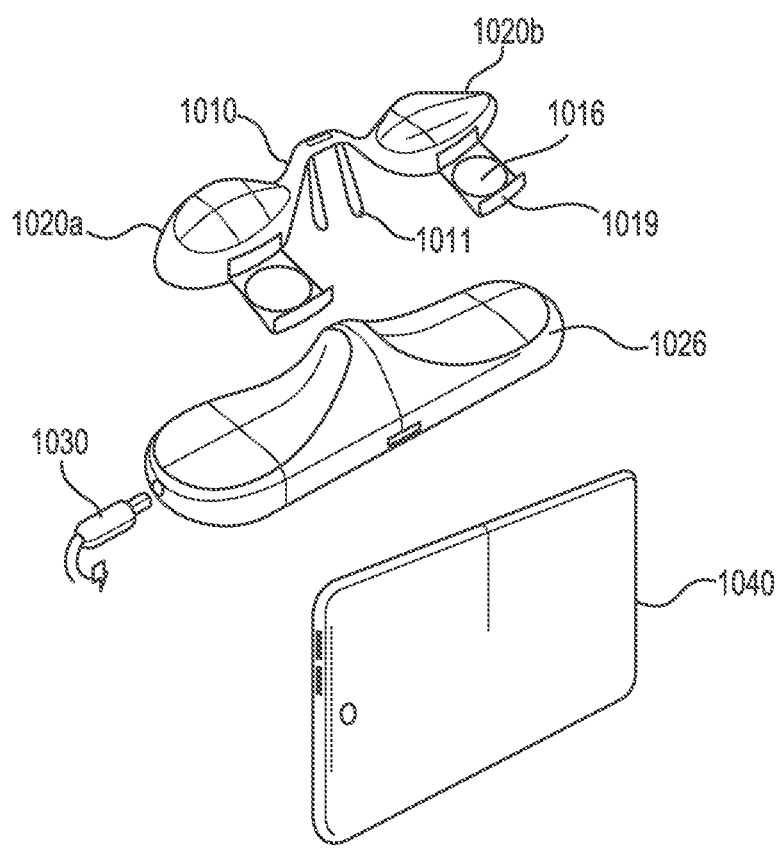
FIG. 10B shows various components of the medical device of FIG. 10A.

A further wearable device 1000 for providing therapy is shown in FIGS. 10A and 10B. The wearable device 1000 may include a frame 1010 configured to be worn on the bridge of the patient's nose similar to a pince-nez. The frame 1010 may include nose grips 1011. First and second treatment pads 1020a, 1020b are coupled to the frame 1010 and are configured to provide therapy to the patient's eyes. In some examples, the first and second treatment pads 1020a, 1020b are integrated into the frame 1010 such that the frame 1010 and treatment pads 1020a, 1020b are a monolithic, single piece structure. The treatment pads 1020a, 1020b may each include a treatment patch 1024 disposed on the underside configured to contact the closed eyelids. In some examples, the treatment patches 1024 may be padded or may be gel pads, and may be removable and disposable or fixedly attached and reusable. Each treatment pad 1020a, 1020b may include an electrode 1022 disposed under the treatment patch 1024, configured to provide therapy to the eye. In some examples, the electrodes 1022 may be adapted for bipolar therapy by providing a compound electrode with two or more separately addressable contacts in close proximity to one another beneath a treatment pad and/or on the same eye, for example located superior and inferior or medial and lateral around the eye. In other examples, the electrodes 1022 may be used in a monopolar fashion and the frame 1010 may include one or more return electrode (not shown) configured to contact the temples, similar to the return electrodes 818 shown in FIG. 8A. In other examples, one or more return electrode may be placed on any portion of the patient's body spaced apart from the eye area, including on or behind the ear, mouth, neck, back, shoulder, chest, back of the hand, arm, etc.

As illustrated in FIGS. 10A-10B, the treatment pads 1020 may be shaped to match the patient's eye socket. The outer perimeter of the treatment pads may include a soft material, such as a foam, to interact with the tissue surrounding the eye to enhance comfort. In some examples the outer perimeter may have a soft but resilient shape that aids in retaining the treatment pads 1020 in the eye socket, with therapy electrodes thereof against the patient's skin, below or above the eye and/or on the upper or lower eyelid, for example. Treatment pads 1020 may be provided in an array of sizes and/or shapes, or may be custom made or custom fitted for individual patients. For example, a central portion of the treatment pads may house electronics and a power source such as a battery, with a replaceable or custom-shapeable perimeter piece thereabout.

Each treatment pad 1020 may include a battery 1016, as shown in FIG. 10B, as well as electronics similar to those described above relative to housing 110. The batteries 1016 may be disposed on trays 1019 that slide into and out of the treatment pads 1020. In some examples, the batteries are replaceable and may be disposable or rechargeable. For rechargeable batteries 1016, the wearable device may further include a charging unit 1026 configured to receive the treatment pads 1020 as shown in FIG. 10B. The charging unit 1026 may have a wired plug 1030. In another example, one treatment pad 1020 carries the battery, whether rechargeable or not, while the other treatment pad 1020 carries the electronics.

A controller 1040 such as an app on a mobile phone, tablet, or computer may be provided for operating, programming and monitoring the treatment pads 1020. The wearable device 1000 may have a wireless connection to the controller 1040 such as a cellular signal, Bluetooth, or other wireless control signal.

Figure 11A:
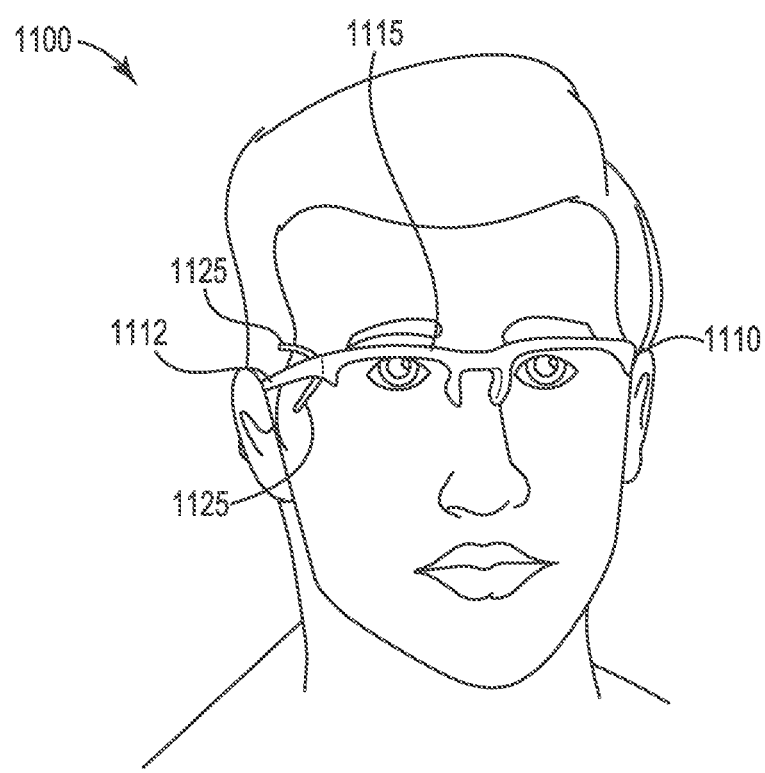
FIG. 11A shows a person wearing another illustrative medical device.

A further wearable device 1100 for providing therapy is shown in FIGS. 11A and 11B. The wearable device 1100 may include a frame 1110 configured to be worn on the patient's face like eyeglasses. The frame 1110 may include two earpieces 1112 configured to extend along the sides of the face and over the ears, and a front piece or bridge 1115 extending between the earpieces 1112 and over the bridge of the nose. In some embodiments, the frame 1110 may include a plurality of prongs 1125 extending from the frame 1110, as shown in FIG. 11A. In some examples, at least some of the plurality of prongs 1125 are hinged and move between a first, contracted position in which the prongs 1125 are directed away from the users face, and a second, expanded position in which the prongs 1125 extend at an angle from the frame 1110 and into contact with the skin. FIG. 11B shows the prongs 1125 in the second, expanded position. In the first, contracted position, the prongs 1125 would be hidden behind the earpiece 1112.

As shown in FIG. 11B, each prong 1125 may have a contact point 1124 configured to contact skin of the patient's face when the frame 1110 is in position on the face. Each contact point 1124 may include an electrode 1122 configured to provide therapy to the patient.

The frame also includes a nosepiece shown generally at 1130, having nose grips 1132, on which are mounted electrodes 1134. The nose grips 1132 may be adjustable, similar to standard eyeglass fittings; rather than two separate prong-shaped nose grips, a V-shaped piece may instead be used in other examples, with one or more electrodes placed on the skin-facing surface of the V-shaped piece. The nosepiece electrodes 1134 may be used relative to the electrodes at 1122, for example, or electrodes carried on the earpieces 1112, such as, for example and without limitation, with earpiece electrodes 1404 or 1504 as shown in FIG. 14A and FIG. 15A, respectively. For example, therapy delivery may use the left or right nosepiece electrode (or the two ganged together) relative to one or the other of the right and/or left earpiece electrodes, as well as combinations, sequences or patterns thereof.

In some examples, the electrodes 1122 may be used in a bipolar fashion by having two separately addressable electrodes 1122 on an eyepiece. In other examples, the electrodes 1122 may be used in a monopolar fashion and the frame 1110 may include one or more return electrode (not shown) configured to contact the temples, similar to the return electrodes 818 shown in FIG. 8A. In other examples, one or more return electrode may be placed on any portion of the patient's body spaced apart from the eye area, including on or behind the ear, mouth, neck, back, shoulder, chest, back of the hand, arm, etc. The electrodes 1122 and/or 1134 may be, if desired, wet electrodes having a wettable polymer or natural fiber, such as a cellulose (for example, similar to Weck-Cel® products) that may be pre-wetted to provide lower impedance tissue-electrode interfaces, or these electrodes may otherwise be any suitable polymer or metal.

The frame 1110 may contain electronics similar to those described above relative to housing 110. The frame 1110 may include at least one battery 1126, as shown in FIG. 11B. The batteries 1126 may be disposed within recesses in the earpiece 1112. In some examples, the batteries 1126 are replaceable and may be disposable or rechargeable. For rechargeable batteries 1126, the frame 1110 may have a charging port 1116.

Similar to the wearable device 1000, the wearable device 1100 may be used with a controller 1040 (shown in FIG. 10B) such as an app on a mobile phone, tablet, or computer, that may be provided for operating, programming and monitoring the electrodes 1122. The wearable device 1100 may have a wireless connection to the controller 1040 such as a cellular signal, Bluetooth, or other wireless control signal.

Figure 12:
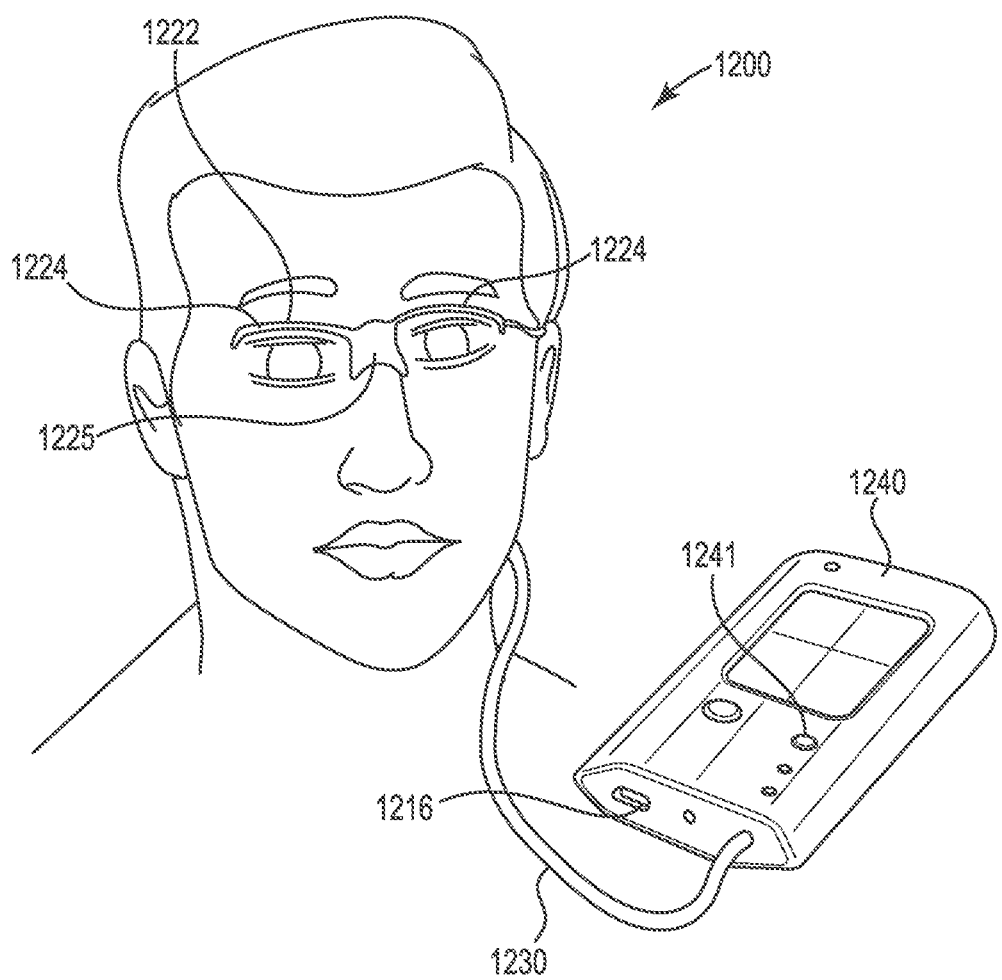
FIG. 12 shows a person wearing another illustrative medical device.
Figure 13:
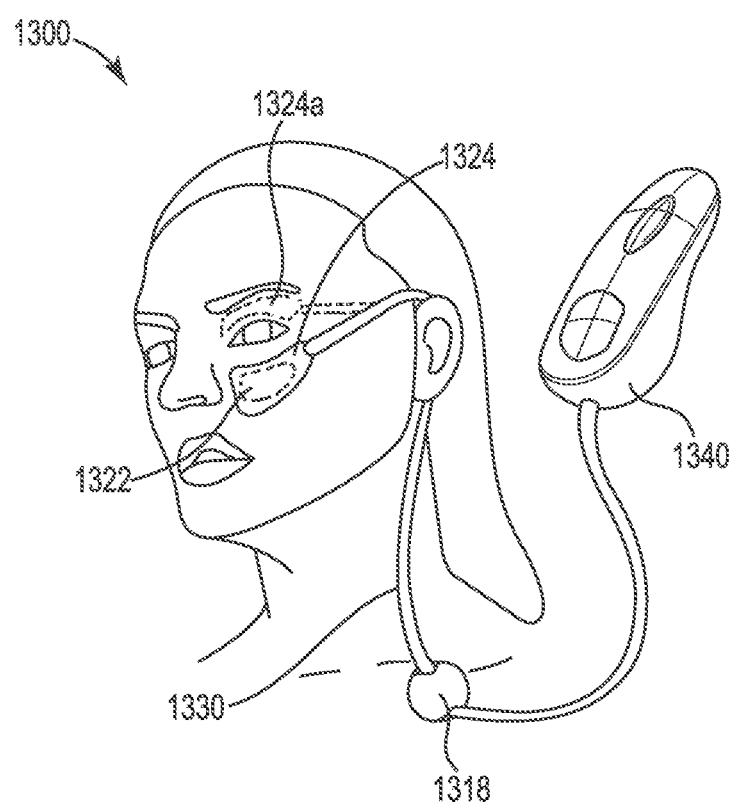
FIG. 13 shows a person wearing another illustrative medical device.

FIGS. 12 and 13 illustrate further examples of wearable devices 1200, 1300 for providing therapy to a patient. The wearable device 1200 shown in FIG. 12 may include first and second treatment patches 1224 and a connector 1230 connectable to a controller 1240 containing circuitry electrically connected to the treatment patch 1224. The treatment patches 1224 may be connected by a bridge portion 1225 configured to be placed over the bridge of the nose. The treatment patches 1224 may be configured to extend over each eye. The treatment patches 1224 may have an adhesive backing configured to adhere the treatment patches 1224 to the skin around the eyes. In some examples, the adhesive may be repositionable and reusable. In other examples, removable double-sided adhesive pads may be provided to adhere the treatment patches 1224 to the face.

The treatment patches 1224 may include one or more electrodes 1222. In some examples, the entire treatment patch 1224 defines the electrode 1222. In other examples, the electrode 1222 may be disposed on the lower surface of the treatment patch 1224 or may be disposed within layers forming the treatment patch 1224. The treatment patches 1224 and electrode 1222 may be similar in material and configuration to treatment patch 824 and electrode 822*a*, 822*b* discussed above. In some examples, one or more return electrode (not shown) may be provided on the wearable device 1200 or as a separate element electrically coupled to the device 1200. The return electrodes may be placed on any portion of the patient's body spaced apart from the eye area, including on or behind the ear, on the temple, on or near the mouth, neck, back, shoulder, chest, back of the hand, arm, etc.

The controller 1240 may contain electronics similar to those described above relative to housing 110. The controller 1240 may be configured to control electrical therapy delivery by the electrode 1222. In some examples, the controller 1240 may include a wall plug. In other examples, the controller 1240 includes a battery, either a disposable battery or a rechargeable battery and a charging port 1216. The controller 1240 may have a touch pad or a plurality of buttons 1241 configured to allow the patient to turn the treatment patch 1224 on and off. In some examples, the controller 1240 may include wireless connectivity to a patient's or physician's cellular phone or tablet (not shown). The connectivity may be through a cellular signal, Bluetooth, or other wireless signal. The wearable device 1200 may be particularly advantageous for treatment with the eyelids open, which may provide for an improved and more convenient experience for the patient. In some examples, the treatment patch 1224 may include padded, foam, or gel regions. For example, the entire treatment patch 1224 may be formed of a foam, padded strip, or gel frame, to provide additional comfort to the patient. The treatment patch 1224 may be formed from a flexible material such as fabric or polymer that is malleable and moldable to the contours of the face.

The wearable device 1300 shown in FIG. 13 may include a treatment patch 1324 and a connector 1330 connectable to a controller 1340 containing circuitry electrically connected to the treatment patch 1324. The treatment patch 1324 may have an adhesive backing configured to adhere the treatment patch 1324 to the skin around the eyes. In some examples, the adhesive is repositionable and reusable. In other examples, removable double sided adhesive pads may be provided to adhere the treatment patch 1324 to the face. In still further examples, the treatment patch 1324 is disposable and removable from the connector 1330. The treatment patch 1324 may be placed under the eye, as illustrated in FIG. 13. In other examples, a treatment patch 1324a may be placed over the eye.

The treatment patch 1324 may include one or more electrodes 1322. In some examples, the entire treatment patch 1324 may define the electrode 1322. The electrode 1322 may be disposed on the bottom surface of the treatment patch 1324 or may be disposed within layers forming the treatment patch 1324. The treatment patch 1324 and electrode 1322 may be similar in material and configuration to treatment patch 824 and electrode 822a, 822b discussed above. In some examples, the electrode 1322 may be used in a monopolar fashion with a return electrode 1318 disposed on the connector 1330 and configured to be in contact with any portion of the patient's body spaced apart from the eye area, including the temple, on or behind the ear, mouth neck, back, shoulder, chest, back of the hand, arm, etc., as described above for return electrode 418 in FIG. 4.

The controller 1340 may contain electronics similar to those described above relative to housing 110. The controller 1340 may be configured to control electrical therapy delivery by the electrode 1322. In some examples, the controller 1340 may include a wall plug. In other examples, the controller 1340 includes a battery, either a disposable battery or a rechargeable battery and a charging port. The controller 1340 may have a touch pad or a plurality of buttons configured to allow the patient to turn the system on and off. Additionally the controller 1340 may allow the patient to activate and deactivate the electrode 1322. In some examples, the controller 1340 may include wireless connectivity to a patient's or physician's cellular phone or tablet (not shown). The connectivity may be through a cellular signal, Bluetooth, or other wireless signal. The wearable device 1300 may be used to treat the eyes while open, which may provide for an improved and more convenient experience for the patient. In some examples, the treatment patch 1324 may include padded, foam, or gel regions. For example, the entire treatment patch 1324 may be formed of a foam, padded strip, or gel frame, to provide additional comfort to the patient. The treatment patch 1324 may be formed from a flexible material such as fabric or polymer that is malleable and moldable to the contours of the face.

FIGS. 14A-14F illustrate another illustrative medical device. In this example, a wearable device 1400 is generally in the form of a frame having an earpiece 1406 and a nosepiece 1410 to be held on the head of a user. The frame carries one or more front electrodes or electrode pads, referred to as electrodes 1402, which are shown adapted for contact with the upper eyelid of the patient/user. In another example, the electrode 1402 may instead by positioned to contact the tissue overlying the nasal bone of the patient/user. In another embodiment, electrodes 1402 can be positioned to contact the forehead of the patient. The electrodes 1402 are carried on an electrode carrier 1402A, which can be adjustable such as with a folding scaffold, foam, wire, or spring-loaded carrier to allow adjustment of the position thereof relative to the patient's upper eyelid or forehead, depending on the desired position.

The earpiece 1406 may include an electrode 1404; such an electrode 1404 may be provided on either or both earpieces. A battery may be held in the earpiece 1406, as indicated by the battery cover shown at 1408. As shown by the top view in FIG. 14B, as well as in 14A, a chamber or island for holding and/or receiving electronics of the wearable device 1400 may be included at 1414 and 1416. If desired, a port 1412 may be provide to receive a USB, micro-USB, or other input.

The nosepiece 1410 may include one or more electrodes for placement on the nose of the user/patient as well, similar to that discussed above relative to FIGS. 11A-11B.

In some examples, a case—similar to a glasses case—may be provided to the user along with the wearable device 1400. Such a case may include an inductive element or antenna and associated driving circuitry configured to provide wireless power to a corresponding receiver circuit (such as an inductive coil or an antenna) in the wearable device, allowing power transfer that can be used to recharge a battery in the wearable device. A charging case structure is disclosed as well in U.S. patent application Ser. No. 16/844,421, filed on Apr. 9, 2020, and titled SYSTEMS AND INTERFACES FOR OCULAR THERAPY, the disclosure of which is incorporated herein by reference.

Figure 14E:
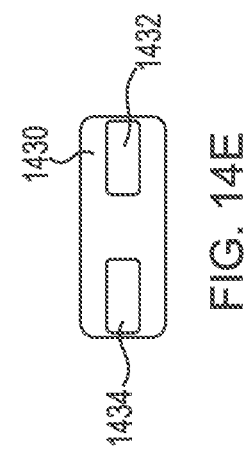
Figure 14F:
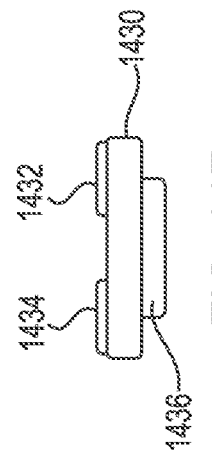
Figure 14C:
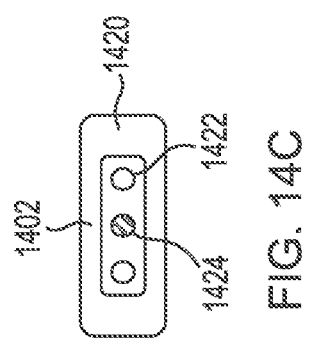

FIG. 14C illustrates details of a removeable form of the electrode 1402. The electrode 1402 may include a gel region 1420 which may be replaceable, or the electrode 1402 may be replaceable in its entirety. For holding the replaceable electrode 1402 in place relative to the wearable device 1400, there may be one or more magnets 1422. For delivery of current, an electrical contact 1424 may be included. The frame 1400 may comprise a receiver shaped to match the design shown in FIG. 14C; the shape, contours, and quantity of magnets and electrodes is merely illustrative. An adhesive or snap fitting may be used instead of magnets, if desired.

An upper or lower eyelid electrode may have a size in the range of about 1 to about 40 mm in length, and about 1 to about 10 mm in width, or greater or lesser in either dimension. As used here, length refers to the dimension lateral to midline when the electrode is applied, and width is the dimension parallel to midline of the patient. In some examples the length of an upper or lower eyelid electrode may be about 10 to about 20 mm and width about 2 to about 5 mm. The area of such electrodes may be in the range of about 1 to about 400 square millimeters, or about 10 to about 200 square millimeters, or larger or smaller. A compound electrode may be, for example, a set of 2 to 4 round electrodes each having an area of 10 to 15 square millimeters, combining to provide about 20 to about 60 square millimeters, though larger or smaller sizes and quantities may be used instead.

A forehead electrode may have a size in the range of about 1 to about 80 mm in length, and about 1 to about 30 mm in width, or greater or lesser in either dimension. In some examples the length of a forehead electrode may be about 15 to about 40 mm, and the width may be about 10 to about 20 mm.

A nose piece electrode may have a size in the range of about 1 to about 20 mm in length, and about 1 to about 20 mm in width, or greater or lesser in either dimension. In some examples the length of a nose piece electrode may be about 4 to about 8 mm in width and about 8 to about 15 mm in length. One or more electrodes on a nose piece may include, for example and without limitation, a single electrode medially placed, or placed to extend on both sides of midline, or may include two or more electrodes including at least one each on the right side and left side of the upper portion of the nose.

Electrode contact surfaces may have any suitable shape including square, rectangular, oval, circular, etc., without limitation. Electrode edges may be beveled or rounded to enhance comfort and avoid potential edge effects with therapy delivery (in which current density is increased at the edges of an electrode-tissue interface). A compound electrode may be used, with multiple individual segments that may move together or which may be provided on separate support apparatuses (wires, spring, foam, etc.), or a single electrode. Longer electrodes may be curved to accommodate anatomical curvature of the upper or lower eyelid/eyeball, and or the cheek or forehead, as the case may be. A concave curvature may be used on the forehead or an eyelid to match to the anatomy in some examples. In other examples, a convex curvature may be used to ensure solid contact across a portion of an electrode. Still other examples may use flat electrodes. In some examples, electrodes for any location (forehead, upper eyelid or lower eyelid) may come in a range of sizes, shapes and/or curvatures, or may be custom built for each patient.

Generally speaking, larger electrodes may be more suitable for use on the forehead than electrodes used on the eyelid, though the overall ranges may remain within the above ranges, more or less. When designing electrodes, various benefits and disadvantages can be considered. For example, a large, flat electrode offers easy manufacture and large area, but may not provide good contact when placed on the skin of a user, which is typically neither flat nor smooth around the eyes. Smaller, button-type electrodes may provide secure contact, but less surface area. Compliant electrodes may be more difficult or more expensive to make, and possibly less durable than rigid options, but may combine greater surface area with better contact. The skin-tissue interface has an impedance that is proportional to the contact area between the electrode and the tissue, among other factors, so smaller surface area may tend to raise impedance. A dry electrode may have a greater impedance in general than a wettable electrode or a gel electrode, but may have longer useful life and greater durability. Multiple smaller electrodes may be provided in a compound electrode and may be used, electrically, separately from one another or as a common pole for the output of current or voltage, and a compound electrode carrier/substrate may be flexible to provide optimal contact for each of the multiple electrodes. The consideration of these factors in selecting and designing electrodes is within the scope of the present invention.

Figure 14D:
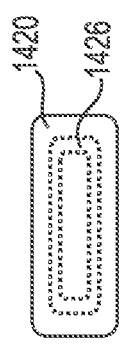

In any embodiment throughout the disclosure dry electrodes may provide advantages. Examples of dry electrodes are discussed, for example, in "Development of printed and flexible dry ECG electrodes", Chlaihawi, A A, etc. Sensing and Bio-Sensing Research, 20 (2018), 9-15. It may be in some examples that a simple metal electrode, such as a silver, medical grade stainless steel, gold or other metal electrode can be used. FIG. 14D shows the front side of one design for an electrode, such as the eyelid-located, or alternatively, forehead located, electrode of FIG. 14A. In this example, a conductive gel surface 1420 is placed over an electrode conductor 1426, which is shown in phantom for illustrative purposes. In an alternative, a dry electrode or electrodes may be used. The electrode conductor 1426 may provide structure to support the gel surface 1420. In other examples, multiple electrodes may be provided on one compound electrode.

FIG. 14E shows a compound electrode 1430, having first and second electrodes 1432, 1434 thereon. In this example, as shown in FIG. 14F, which is a side view of the electrode shown in a frontal view in FIG. 14E, it can be seen that the first and second electrodes 1432, 1434 extend away from the surface defined by the body of the compound electrode 1430, which may aid in obtaining good contact against the user's skin. The first and second electrodes 1432, 1434 may be dry electrodes, wettable electrodes, or may have gel pads, either individually or across the whole surface of the compound electrode 1430.

For purposes herein, an electrode assembly may be either a single electrode or a compound electrode having two or more individually addressable electrodes thereon. Any of the examples herein that show a single electrode should be understood as also disclosing the use of a compound electrode, rather than a single electrode, having two or more individually addressable electrodes thereon. The back side of the compound electrode 1430 is shown in the side view of FIG. 14F as well, and includes a coupling protrusion 1436 extending therefrom, sized and shaped to be received in a corresponding slot or port of a wearable device.

In some examples, and in particular in each example showing a frame-type wearable instrument (such as FIGS. 11A-B, 14A-B, 15A-B, 16 and 17A), one or more electrodes may be part of a spring-loaded assembly that will apply pressure between the wearable device and the electrode to facilitate contact with the patient's skin. For example, a spring loaded accordion structure, or a foam or sponge piece, one or more miniature leaf springs (an arc-shaped spring structure) may be used as an electrode carrier (FIG. 14B, at 1402A, FIG. 15B, at 1502A) or in as a coupling protrusion (FIG. 14F, at 1436). In some examples, the electrodes may be provided on a pivoting or swivel structure to aid in obtaining good contact, for example, nose grips (FIG. 10A/B, at 1011, FIG. 11B at 1132), or prongs (FIG. 11A, at 1125) may be coupled to a frame with a pivot or a swivel. The electrodes may come in a range of sizes and/or shapes, and support structures to hold the electrodes in place may be adjustable or may come in a range of sizes to allow a physician to tailor the device to a particular patient's anatomy, similar to how an optometrist can fit glasses to a user. In some examples, the overall frame may come in a range of sizes, or may be designed with replaceable portions, such as for contacting the bridge of the nose or the ears, or the arm extending from the ear, to adjust for individual patient anatomy.

FIGS. 15A-15B show another illustrative medical device. In this example, the wearable device 1500 is generally in the form of a frame having an earpiece 1504 and a nosepiece 1510. The frame carries one or more front electrodes or electrode pads, referred to as electrodes 1502. The electrodes 1502 are carried on an electrode carrier 1502A, which can be adjustable such as with a folding scaffold, foam, wire, or spring-loaded carrier to allow adjustment of the position thereof relative to the patient's upper eyelid or forehead, depending on the desired position. The earpieces 1504 may include an electrode 1506, and one (or both, if desired) earpiece 1504 may include an attached or removeable wire 1508 that may be used to couple to a return electrode placed elsewhere on the user (such as on the torso, neck, limb, wrist, or hand). Alternatively, the wire 1508 may couple to a pulse generator or a charger, which may also have a return electrode thereon, and which may also house circuitry and/or a power supply for the delivery of therapy.

In some examples (including at least that of FIGS. 15A-15B, but also others having a remote electrode tethered via a wire to a frame), the frame may carry electronics for generating therapy signals, and a remote electrode can be carried on a housing that holds replaceable or rechargeable batteries. Such a configuration of a remote electrode on a housing carrying a power source may be used in any other example disclosed herein as having a remote electrode, providing the benefit of reduced weight on the frame itself and facilitating use of heavier batteries (or relatively cheap, standard size batteries, such as AA, AAA or 9V batteries) that would not require frequent recharging or replacement.

In this example, the nosepiece 1510 is somewhat larger and may include a slot or chamber for receiving a battery cell or cells, or a battery pack, such as one or more button batteries. The battery may be a primary, non-rechargeable cell, or may be rechargeable, if desired. The nosepiece 1510 may also carry electronics for the therapy device as well, if desired. As shown as well in the top view of FIG. 15B, regions 1512, 1514 may be enlarged to receive electronics for the device 1500. The nosepiece 1510 may include one or more electrodes for placement on the nose of the user/patient as well, similar to that discussed above relative to FIGS. 11A-11B.

Figure 16:
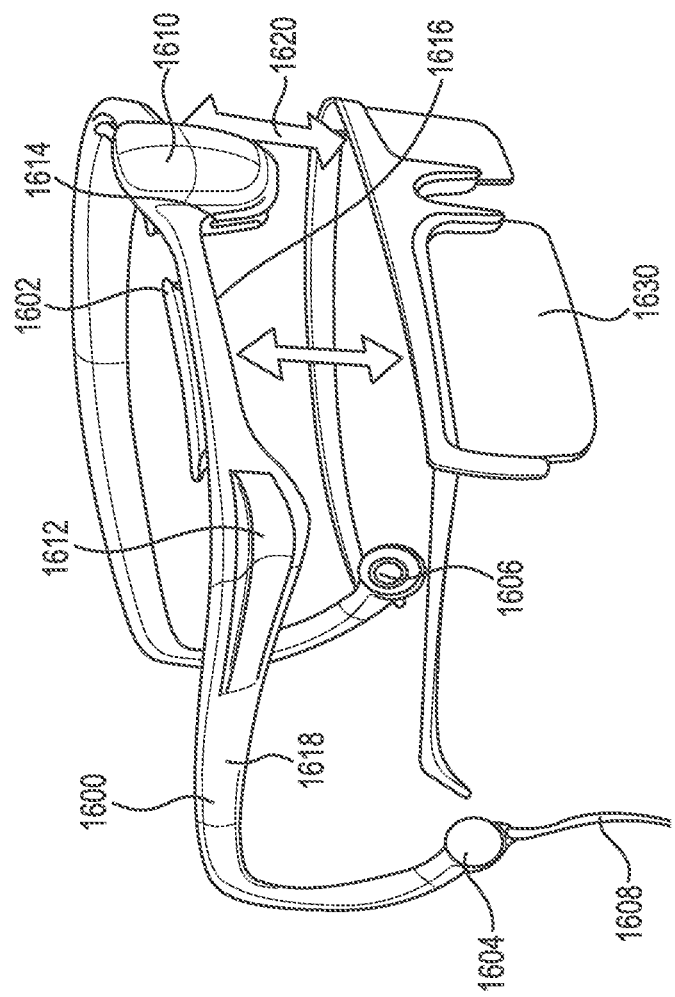
FIG. 16 shows another illustrative medical device.

FIG. 16 shows another illustrative medical device. In this example, a treatment device 1600 is configured to be placed over/on a glasses frame 1630, as indicated by arrow 1620. The treatment device 1600 may be made of a flexible polymer to receive the glasses frame 1630 in a slot 1614 that can be formed along the nosepiece 1610 and may also extend along region 1616 and, optionally, region 1618, as well as in or near the earpieces 1604.

The treatment device 1600 is shown carrying electrodes 1602 (again, in an example, suitable for placement on the upper eyelid or, alternatively, on the forehead) and including earpieces 1604, which may each carry an electrode 1606. One or more of the earpieces 1604 may include a wire 1608 for coupling to a remote return electrode or a pulse generator or charger, as desired. Again, the treatment device 1600 may include enlarged regions 1612 for housing or receiving electronics therein. If desired, the nosepiece 1610 may be adapted to receive or house one or more battery cells or a battery pack. As used herein, a battery pack may comprise a frame that receives one or more battery cells in a customized manner to make for easy placement and removal from a wearable medical device. The nosepiece 1610 may include one or more electrodes for placement on the nose of the user/patient as well, similar to that discussed above relative to FIGS. 11A-11B.

FIGS. 17A-17D show another illustrative medical device. The example here takes the form of a wearable device 1700 generally in the form of a frame, similar to an eyeglasses frame and adapted to receive lenses 1720, which may be prescription lenses that correct vision, if desired. As generally shown, a front piece having a nose piece 1714 and carrying an electrode or electrode pad 1702 is coupled to first and second arms that extend to earpieces 1706 that are shaped to contact and rest, at least partly, on the ear(s) of the user; the earpieces 1706 may, in some examples, at least partly wrap around the ear of the user. The lenses may be placed as shown at 1722 in a slot 1716 configured to receive them in a friction fit or snap fit fashion, for example. The lenses may also, or instead, provide light protection, for example, making the wearable device 1700 suitable for use as sunglasses. Lenses 1720 may be omitted in other examples.

Figure 17A:
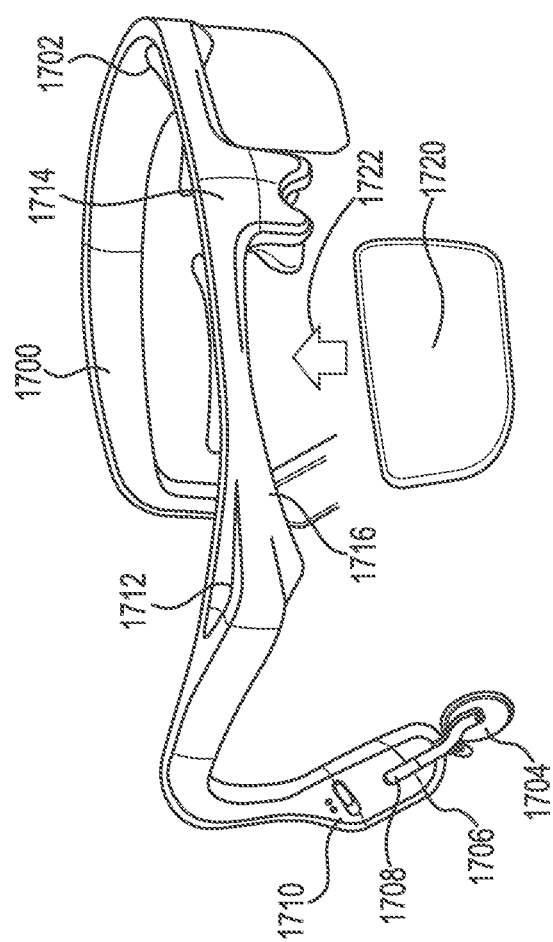

As shown in FIG. 17A, the wearable device 1700 includes electrode pads 1702, adapted for placement on the upper eyelid or, alternatively, on the forehead. The electrode pads 1702 may comprise one, two, or more addressable electrical contacts (which may be separately addressable and/or ganged together for output or sensing purposes), and may be permanently fixed, disposable, or may include electrical contacts surrounded or covered by a replaceable element such as a gel pad, a wettable element (such as a cotton pad), or may simply be electrodes without added layers/padding. The electrode pads 1702 may be adjustable, either or both of in terms of the shape of the pad (to match the user's forehead) and in terms of how each is juxtaposed relative to the overall device 1700 (to accommodate different face sizes and shapes). Electrical wiring (not shown) can run through the eyeglasses-type frame shown from the power supply to the electronics and electrodes, wherever each is positioned; the electrical wiring may be selected to be of relatively larger gauge to provide structural support and/or adjustability, if desired, or may be lightweight with separate metal structures provided for structural support and/or adjustability. The nosepiece 1714 include one or more electrodes for placement on the nose of the user/patient as well, similar to that discussed above relative to FIGS. 11A-11B.

In another example, the earpieces 1706 may be replaceable/swappable, while the remainder of the frame shown is custom to a given patient, such as by using 3D printing or other tailored manufacturing process for the rest of the device 1700, allowing the use of modular, pre-programmed or powered earpieces (assuming the electronics and/or power source are carried there). For example, rather than having a user with impaired eyesight attempt to swap out small batteries (similar in size to those used in hearing aids for example), the user could change out an entire earpiece, which may be easier to do. In some examples, the device 1700 may have only one electrode pad 1702, such as for a user needing treatment on only one eye. The shape of each earpiece and the arm extending thereto may be customizable, using methods, materials and designs known for eyeglasses.

Earpieces 1706 may carry electrodes 1704 that are held by flexible, or adjustable/shapeable, arms 1708. One or both earpieces 1706 may include a switch 1710 for turning the device on/off, as well as indicator lights that may be used to display status (on/off/error, for example). Expanded regions 1712 are optionally provided on the device 1700 and may receive or hold electronics. A nosepiece 1714 is again provided, and may be sized/shaped to hold or receive a power supply, such as one or more batteries or a battery pack for the system, with the batteries being either rechargeable or non-rechargeable.

In other examples, the earpieces may house the power supply and electronics. For example, earpiece 1706 is shown in the foreground of the Figure; a second earpiece is obscured from view by lens 1720. Earpiece 1706 may have the switch 1710 and electronics for the system, with a rechargeable or non-rechargeable (permanent or replaceable) battery carried in the obscured earpiece, which may serve an advantage by reducing the weight of the device 1700 carried on the nose of the user. As noted, power supply and electronics may be placed at 1712/1714, which would put more weight on the user's nose, potentially providing a more secure placement of the electrode pad 1702. Other arrangements of the power source/battery and electronics may be used instead.

One or both earpieces may include an inductive recharging circuit (in the case of a device having a rechargeable battery), though such inductive recharging circuit may also be elsewhere such as in the optional expanded regions 1712 and/or nosepiece 1714, for example. Additionally, or alternatively, a port may be provided on any of the earpiece 1706 or front portion or nose piece of the device to receive a wire plug, such as a micro-USB plug, to facilitate recharging of a battery and/or reprogramming of a therapy output circuit. In some examples, a wireless communication circuit may be provided, such as a Bluetooth or Bluetooth Low Energy circuit, to allow telemetry with a programming device such as a clinician programmer or patient controller, either of which may be a dedicated device or may be a general purpose device (such as a smartphone or tablet computer) having a specific software application thereon usable for programming purposes.

Figure 17D:
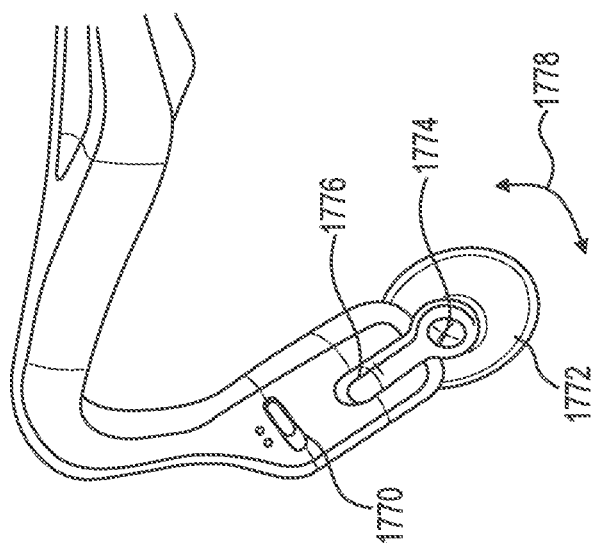

FIGS. 17B-17D show alternative earpiece configurations. As shown in FIG. 17B, the earpiece 1730 may couple to an electrode at an edge thereof, with a first pivot at 1734 in the form of a ball joint allowing movement of the electrode 1732 to match the contour of the patient's skin. A second pivot is provided at 1736, allowing motion within a range illustrated at 1738. The combination of pivots 1734, 1736 may aid in comfortable and secure positioning of the electrode 1732.

FIG. 17C shows another example. Here, the earpiece 1750 includes an electrode 1752 that can be snapped into a slot for receiving it and coupled to the earpiece 1750 by a wire/tether 1754. In this example, the electrode 1752 may be a replaceable element and/or may have a replaceable sticky interface thereon. Thus the electrode 1752 can be carried on the earpiece 1750 when not in use, and removed from its slot for use.

FIG. 17D shows another alternative earpiece. Here, the earpiece 1770 is coupled to an electrode 1772 with a ball joint 1774, which can be used to orient the electrode 1774 relative to the contour of the patient's skin, achieving good and comfortable contact across the area of the electrode 1774. A second pivot is provided at 1776, allowing motion within a range shown by arrows 1778.

Several examples herein, including that shown in FIG. 1, some versions of FIGS. 11A-11B, FIGS. 12, 14A-14F, 15A-15B, 16, and 17A-17D, may be characterized by the omission of any electrode on the face of the user below the palpebral aperture. Certain prior attempts at electrical therapy delivered to the eye may include electrodes disposed around the eye, superior as well as inferior to the palpebral aperture, however, such therapy delivery may focus energy toward the anterior of the eye, rather than directing current deeper into the eye where the maculae and/or optic nerve can receive delivered energy. Thus, and for example, earlier or alternative devices that use anterior-placed electrical stimulus to provide therapy to eye and/or surrounding tissues may be differentiated in these example embodiments. Other examples, as shown above, may include electrodes about the eye opening.

The following description applies to any of the above described wearable device 100, 200, 300, 400, 500, 600, 700, 800, 900, 1000, 1100, 1200, 1300, 1400, 1500, 1600, and/or 1700, but for simplicity, the reference numbers for wearable device 100 will be used. The treatment patches 124 may be disposable or reusable. The reusable treatment patches 124 may be permanently attached to the wearable device 100. The controller 140 may provide control of the pattern of electrode 122 activation as well as an on/off switch, or just provide an on/off switch. The wearable device 100 may utilize rechargeable batteries, disposable batteries, or a power cord. The rechargeable batteries may be charged using a USB charging cord or an induction unit. Any of the treatment patches 124 discussed above in any embodiment may be dry or wet. Therapy may be delivered in bipolar fashion (such as using first and second electrodes both disposed about a single eye of the user) or monopolar fashion (such as using a first electrode on the eye of the user and a second, return electrode distant from the eye. The return electrode for any embodiment discussed above may be placed on any portion of the patient's body spaced apart from the eye area, including on or behind the ear, on the temple, on or near the mouth, neck, shoulder, back, chest, back of the hand, arm, etc.

In some embodiments, the wearable device 100, 200, 300, 400, 500, 600, 700, 800, 900, 1000, 1100, 1200, 1300, 1400, 1500, 1600, and/or 1700 (and variations, systems or components thereof disclosed herein) and/or portions thereof, may be made from or include plastics, metals, alloys, fabrics, composites, or combinations thereof. As variously stated above, the wearable devices 100, 200, 300, 400, 500, 600, 700, 800, 900, 1000, 1100, 1200, 1300, 1400, 1500, 1600, and/or 1700 may carry or contain, or be connected, such as by a wired connection, to electronics as described above relative to housing 110 including, for example, a microcontroller, memory, sensing input circuitry, and output circuitry for generating any suitable form of output, including voltage, current, light, mechanical energy, etc.

The above examples may be used for delivering ocular modulation therapy. As used herein, "ocular modulation" refers to the treatment of the eye with a signal, delivered non-invasively, or minimally-invasively, to achieve a therapeutic benefit. Therapeutic benefit may include, for example and without limitation, improving or altering blood flow, upregulating or downregulating synthesis, degradation, binding, release or activity of proteins, enzymes, DNA, RNA, polysaccharides or other endogenous physiological or pathological biomolecules; and/or upregulating, downregulating, activating, deactivating physiological or pathological biopathways, etc. Ocular modulation may be combined with the administration of pharmaceuticals, exogenously derived biomolecules, cell therapy, or photo-, electro- or magneto-reactive or active particles, such as nanoparticles, before, during or after an electrical signal is applied.

In some examples, the devices and systems disclosed herein are suited for use in conjunction with exogenous and/or endogenous stem cell transplantation therapies. For example, a method may comprise delivery of electrical stimulation before, during, or after stem cell transplantation to improve cell survival, integration, repair and/or replacement. In some illustrations, the use of methods and systems disclosed herein may enhance native cell survival, transplanted cell survival, transplanted cell integration, and functional synapse formation and/or axon regeneration. For example, a transplanted or implanted cell scaffold be encouraged to successfully integrate with the retina by the application of electrical fields, including by the use of static or varying fields, wherein variation may include any of spatial or temporal variation. Non-limiting examples of endogenous stem cell types which may be suitable for transplantation in combination with systems or devices of the present invention include Müller cells, retinal pigment epithelial cells (RPE cells) and ciliary pigmented epithelial cells (CPE). Non-limiting examples of exogenous stem cells suitable for transplantation according to some embodiments of the invention include neural stem cells (NSCs), mesenchymal stem cells (MSCs) derived from bone marrow, adipose tissue or dental pulp and stem cells from the inner cell mass of the blastocyst and induced pluripotent stem cells (iPSCs). See, for example, "Using Electrical Stimulation to Enhance the Efficacy of Cell Transplantation Therapies for Neurodegenerative Retinal Diseases: Concepts, Challenges, and Future Perspectives", Abby Leigh Manthey, et al., Cell Transplantation, Vol. 26, pp. 949-965, 2017.

In some examples, combination of therapy systems of the invention with biological or pharmaceutical agents may provide improved efficacy or reduced side effects associated with such biological or pharmaceutical agents when administered alone. Pharmaceutical agents currently used to reduce the growth of new blood vessels in wet AMD include anti-angiogenics such Bevacizumab (Avastin®), Ranibizumab (Lucentis®) and Aflibercept (Eylea®), etc. While the benefit of these agents for mitigating symptoms associated with wet AMD are known, these also may have side effects including increased eye pressure, inflammation of the eye and others. A benefit of systems disclosed herein includes modulation of cytokines and other endogenous inflammatory factors involved in the inflammation process. In some embodiments it is foreseen that administration of anti-angiogenic agents or other pharmaceuticals in combination with electrical therapy applied simultaneously with, before (e.g. 1, 2, 12, 24, 36, 48 and/or 96 or more hours before), or after (e.g. 1, 2, 12, 24, 36, 48 and/or 96 or more hours after), injection of such anti-angiogenics, at stimulation parameters used herein, may beneficially improve the efficacy and/or reduce the likelihood of side effects associated with administration of such agents.

Several different modes of energy delivery are disclosed, including mechanical (such as sonic energy, including for example, ultrasound), light-based (such as by the delivery of collimated or non-collimated light using, for example, a laser, a light emitting diode, etc.), electrical (such as by the delivery of an electrical signal), and/or magnetic (such as by generating a magnetic field or fields), and combinations thereof. In some examples, one mode of therapy delivery is used, while the same or a different mode of sensing is used to monitor therapy delivery. One component of several examples is the use of configurations that are adapted to provide enhanced tissue contact, enhanced therapy delivery location, improved efficiency of energy delivery, targeted therapy, reduced likelihood of tissue injury or irritation, and/or improved patient comfort and/or compliance.

In some examples, electrical stimulus may also be provided to facilitate diagnostics. For example, an electrical stimulus may be generated as a controlled voltage, and current that flows may be measured, or voltages sensed at non-anode/cathode electrodes may be measured, to determine impedances and/or tissue contact characteristics. Generally speaking, lower impedance indicates better skin contact and better energy or current transfer characteristics.

Various features for delivering therapy may be understood by review of, for example and without intending limitation, U.S. Pat. No. 7,251,528 to Harold, U.S. Provisional Patent Application Ser. No. 62/739,810, filed Oct. 1, 2018, and titled SYSTEM AND METHODS FOR CONTROLLED ELECTRICAL MODULATION FOR VISION THERAPY, U.S. Provisional Patent Application Ser. No. 62/774,093, filed on Nov. 30, 2018, titled HEAD WORN APPARATUSES FOR VISION THERAPY, and U.S. Provisional Patent Application Ser. No. 62/832,134, titled SYSTEMS AND INTERFACES FOR OCULAR THERAPY, the disclosures of which are incorporated herein by reference as showing waveforms, structures, apparatuses and systems for delivery of ocular modulation. Such disclosures also provide additional options and implementations of the electronics of the devices and systems herein.

In some examples, a bipolar electrode approach is taken, without the use of a remote return electrode. In other examples, a monopolar therapy can be delivered, using one or more electrodes located on an eyelid or close to the eye as anode or cathode, and a remote electrode elsewhere on the user, such as on the head, torso or a limb. For example, a return electrode may be on the user's arm, hand, shoulder, chest, back, neck, mouth, on or behind the ear, or temple of the user. A biphasic therapy may be delivered, allowing for charge balancing of the output and making use of each electrode as both anode and cathode during therapy output. Alternatively, a monophasic therapy may be provided, making use of particular electrodes only as anodes or as cathodes; to avoid post-therapy shock (similar to a static shock), the electrodes may be grounded for a period of time to drain any residual voltage on the tissue/electrode interface. In still further examples, both biphasic and monophasic therapy are delivered, for example, in a patterned therapy using each type of therapy delivery in alternating or cyclic fashion. In an example, monophasic therapy may be provided for a fixed period of time, with subsequent phase reversal and further delivery for another fixed period of time, avoiding over-polarization, which could lead to, for example, muscle recruitment or may encourage corrosion or other damage to the electrode-tissue interface.

Waveshape may vary. If desired, sinusoidal, triangular, ramped (up or down), exponential (up or down), or square waves may be delivered in any of current, voltage, or power controlled outputs. For example, a current controlled output may provide a square wave of constant current for its duration. In another example, a voltage controlled output may take the form of an exponentially decaying output. Other combinations and shapes may be used if desired. In some examples, an output circuitry of the electronics module may be configurable between a first configuration that delivers current controlled outputs and a second configuration that delivers voltage controlled outputs. For example, a first feedback loop may be provided that monitors voltage across the output electrodes (for voltage control), while a second feedback loop monitors voltage across a resistor (for current control) that is in series with the output electrodes, and the controlling circuitry such as a microprocessor, ASIC, or state machine, can be programmed to select one or the other of the feedback loops to use.

In some examples, the output waveform may comprise a modulated carrier wave, such as a modulated 1 Hz to 1 MHz output, shaped as a square wave; higher or lower frequencies may be used. In an example, a carrier wave takes the form of a square wave with a frequency of 1 kHz to 40 kHz and 50% duty cycle, modulated by an envelope signal of a lower frequency as discussed in U.S. Pat. No. 7,251,528, the disclosure of which is incorporated herein by reference. The duty cycle may be anywhere from 1% to 100%, if desired. The envelope may be a square wave in the range of about 1 to about 100 kHz, more preferably about 1 to about 1000 Hz, or about 1 to 400 Hz. In another example, the envelope may be at a selected on of 10, 20, 30, 40, 50, 100, 200, 300, 500 or 1000 Hz; other envelope frequencies may be used. In still another example, the user may receive a series of different frequency outputs, by varying the envelope frequency and/or varying the carrier frequency. The carrier wave or the envelope may be sinusoidal instead, if desired, or may have a different shape such as triangular, ramped, etc. In some examples, additional factors may be programmable parameters, such as duty cycle, pulse width of the carrier signal or envelope signal. In an example, a monopolar output is provided, with periodic changing of the polarity to maintain charge balance at the tissue interface. For example, some embodiments of a wearable therapy apparatus provide a stimulus output as a first train of monophasic output pulses of a first polarity, and a second train of monophasic output pulses of polarity opposite the first train. In other examples, therapy output may be allowed to leave a residual charge imbalance.

In another example, a therapy signal is provided with a frequency of about 1 Hz to about 1 MHz, and the combination of carrier and envelope is omitted. For example an output may be provided as a biphasic square wave with a frequency in the range of 10 Hz to 20 kHz, or about 100 Hz to about 15 kHz, with the output delivered for a fixed period of time such as 1 millisecond to about 1 hour, or about 100 milliseconds to about 30 minutes. The waveform may be delivered repeatedly, at fixed or random intervals, and may take other shapes including triangular, sinusoid, etc. Therapy signals may be delivered with a soft turn-on or ramp, in which the therapy output signal is ramped up from a starting level (such as 0 volts or 0 amps) up to the desired therapy level over the course of a few milliseconds to a few seconds, or longer. Other parameters including pulse width, off time, polarity switching frequency (if used), etc. may vary as well.

A programmable amplitude may be set as well using, for example, power, current or voltage as the controlled variable. In some examples, current may be delivered in the range of about 0.1 to 2000 microamperes, or in the range of about 1 to about 1000 microamperes, or in the range of about 300 to 500 microamperes, using any of the above noted parameters for waveshape, frequency, duty cycle, etc.

Other specific settings may be used, including those disclosed and discussed in further detail in U.S. patent application Ser. Nos. 16/589,383, 16/697,689, and/or 16/844,421, U.S. Pat. No. 7,521,528, and/or U.S. Provisional Patent Applications Nos. 62/867,421, 62/873,450, the disclosures of which are incorporated herein by reference.

The user may be allowed to freely modify parameters, or access may be restricted to a clinician user, or it may be that the user can modify parameters within a narrower range controlled by a clinician. For example, a clinician may be enabled to set current in a range of 1 to about 1000 microamperes, while the user can only modify the current, once set by the clinician, within a range of plus/minus 100 microamperes, or more or less. In some examples, the user may not be allowed to change parameters. A method example may comprise the steps of a user donning any of the preceding wearable devices, or alternatives thereto, to place the one or more electrodes thereof at a desired, instructed, or therapeutic position, and activating circuitry of the wearable devices, when so provided, to deliver therapy. Still another method example comprises any of the preceding wearable devices issuing therapy pulses via the electrodes thereof for purposes of treating, reversing, preventing, arresting, or otherwise addressing a disease of the eye or surrounding tissues.

In some examples, a closed loop approach may be taken wherein sensing circuitry in the apparatus is configured to sense select parameters of therapy delivery or sense other parameters, such as biological events. For example, it has been shown that users may experience flashes of light, known as phosphenes, during therapy. To allow a user to perform ambulatory or other activities, phosphenes may be avoided by having the device sense for phosphenes and reduce power output when phosphenes are sensed to limit the impact to a user's visual experience. Another approach may be to occasionally or periodically test a user's phosphene threshold, such as at the start of a therapy session, and then set therapy parameters to use duty cycle, amplitude, current density, or other factor so therapy stimuli is delivered at a level that is below the phosphene threshold. Such testing may further include having a user move his or her eye to different positions during threshold testing (i.e., looking up, down, left or right) by issuing one or more commands to the user to modify eye position during phosphene threshold testing. Avoidance of phosphenes may also be useful for patients having other conditions, such as epilepsy or migraines, which may be triggered or exacerbated by exposure to flashes of light.

The ability to select from various pairing of electrodes may be useful to provide therapy targeting separate conditions by selective use of the electrodes. For example, glaucoma is typically associated with fluid transport structures in the eye that are more superficial, anatomically, than structures associated with a condition such as macular degeneration. Therefore, in an example, relatively more closely spaced electrodes, or bipolar therapy regimens, may be used to treat glaucoma, while more greatly spaced electrodes, and/or monopolar therapy regimens may be used to treat macular degeneration, for a user having or at risk for both conditions.

In a still further example, a current flowing between two electrodes on one eyepiece may be useful in glaucoma patients to cause contraction or expansion of the ciliary muscle regions, opening the iris root and facilitating drainage through the trabecular meshwork. In some examples, a current applied by an eyepiece may energize a stent placed in the trabecular meshwork to aid fluid flow, or may energize a device placed elsewhere in the eye to cause other beneficial therapeutic effects such as heating, light or electrical stimulus affecting neural or other structures in the eye. In examples it is envisioned the bipolar electrode positioning around an eyepiece can provide selected stimulation to rehabilitate an atrophied ciliary muscle before or after implantation of an artificial intraocular lens. In still other examples, other structures in the head may be targeted, such as the optic nerve and/or targets in or around the brain, the sinuses, or the eye.

Multiple therapy patterns or programs may be set for a device. For example, the electrical components may comprise a state machine or microprocessor with stored states or stored instructions, respectively, to deliver pre-selected therapy patterns or types. Therapy patterns may be defined according to which electrodes are selected for use (and in which role—ground, anode, cathode, etc.), and output characteristics for each output channel (pulse width, frequency, amplitude, relative amplitude, pulse shape, duty cycle, interpulse intervals, burst patterns, etc.). Such patterns or programs may be set by a physician during a programming session using, for example, a clinician device such as a mobile phone, table or computer, or a dedicated programmer device, as desired.

While the above description generally shows the use of a battery or rechargeable battery, other power sources may be used. In some examples, a battery may be omitted and a capacitor or supercapacitor used instead, allowing charging and discharging over time. For example, a receiving antenna or inductive coil may receive energy output by a remote device and the received power can be used to charge a capacitor. Once the capacitor is charged to a desired level, the capacitor can be discharged to deliver therapy to the user. A determination that the capacitor is at the desired level may be made by, for example, having a comparator in the system to compare to a reference voltage, or by having a silicon-controlled rectifier that, once the desired voltage level is reached, will close a switch allowing discharge of the capacitor and open again once the capacitor is discharged to at least a threshold amount.

As noted, the control circuitry architecture may comprise a microcontroller, microprocessor, or a state machine, as desired and as suitable to the particular needs of a system. Volatile or non-volatile memory may be included to store various parameters, settings and data, such as patient information, therapy programs that may be used, therapy parameter limits, diagnostic and/or usage history information, etc. Analog to digital conversion circuitry may be provided for converting sensed signals, such as a sensed impedance, sensed phosphene, sensed eye movement, output from an accelerometer, etc. to digital data for analysis and/or storage. Digital to analog conversion circuitry may also be included to allow, for example, a control signal to be converted from a digital format to an analog output that controls one or more of frequency, waveshape, amplitude, etc. of an output stimulus or therapy.

While some examples the apparatus may sense when it is being worn by a patient, such as by sensing impedance between two electrodes, by sensing a thermistor output, or any other suitable sensing approach. In an example, the user may turn the device "On" with a switch, but therapy will only initiate when the control circuitry determines that stimulus electrodes have been placed on patient tissue with good contact (that is, lower impedance) to avoid inadvertent shocking when the device is being adjusted, moved, donned, removed, etc.

In some examples, the electrical components used to deliver electrical therapy via the electrodes may include a multi-channel topology. Separately addressable voltage and/or current sources may be used, having one source, two sources, or as many such sources as there are electrodes, if desired, or even with more sources than electrodes. Some sources may output current (current sources) or drain current (current sinks), while others may provide positive or negative voltages relative to system ground/reference. In some examples, there may be dedicated voltage or current circuits for each electrode while in other examples, a bank of voltage or current generating circuits may be coupled by an array of switches or a multiplexor to the output electrodes, allowing therapy generating circuits to be ganged together on a single output electrode or spread out across a number of electrodes. A single channel output may be used instead, if desired.

Miniaturization of a neural stimulator has been taken to great lengths including providing communication, pulse output, power storage and/or control circuitry in implantable devices of just a few grams and cubic centimeters, such as shown in U.S. Pat. Nos. 5,193,540 and 8,612,002, the disclosures of which are incorporated herein by reference. Moreover, the provision of multiple channel outputs has been shown as well, including for example in U.S. Pat. Nos. 5,643,330 and 6,516,227, the disclosures of which are incorporated herein by reference. The circuitry and capabilities of the systems disclosed in these patents may be integrated into a number of the above embodiments as desired.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The claim's scope is, of course, defined in the language in which the appended claims are expressed.

What is claimed is:

1. A wearable device for providing therapy to a patient, the device comprising a frame having a front piece and first and second arms extending therefrom, the front piece including a nosepiece and carrying at least one front electrode or front electrode pad thereon, the first and second arms extending from the front piece to first and second earpieces, respectively, which are shaped to contact and rest, at least partly, on the ear of a user, at least one of the earpieces carrying an earpiece electrode, the device further comprising a control circuit and a power source, the control circuit configured to issue electrical signals through the front electrode or front electrode pad and the earpiece electrode to provide therapy to the eye of a user; wherein the earpiece electrode is positioned on or behind the ear when the wearable device is worn by the user; and the front electrode or front electrode pad is adjustably coupled to the front piece to be held against an upper eyelid of the user.

2. The wearable device of claim 1 wherein the front electrode or front electrode pad is coupled to the nosepiece.

3. The wearable device of claim 1 characterized by the omission of any electrode on the face of the user below the palpebral aperture.

4. The wearable device of claim 1 wherein the power source is a rechargeable battery.

5. The wearable device of claim 1 wherein the power source is a replaceable battery.

6. The wearable device of claim 1 wherein the control circuit is contained in the first earpiece, and the power source is contained in the second earpiece.

7. The wearable device of claim 6 wherein at least one of the first and second earpieces are detachable.

8. The wearable device of claim 1 wherein the front piece comprises a first expanded portion and a second expanded portion on either side of the nosepiece, the control circuit being contained in the first expanded portion and the power source being contained in the second expanded portion.

9. The wearable device of claim 1 wherein the control circuit is contained in the nose piece.

10. The wearable device of claim 1 wherein the power source is contained in the nose piece.

11. The wearable device of claim 1 wherein the first and second earpieces are shaped to at least partly wrap around the ears of the user.

12. The wearable device of claim 1 wherein the earpiece electrode is held on a flexible or moveable arm.

13. The wearable device of claim 1 wherein the front piece is configured to receive first and second lenses.

14. The wearable device of claim 1 further comprising an on/off switch actuatable by a user and carried on one of the first and second earpieces.

15. A method of treating a patient comprising:
a patient donning a wearable device for providing therapy to the patient, the wearable device including a frame having a front piece and first and second arms extending therefrom, the front piece including a nosepiece and carrying at least one front electrode or front electrode pad thereon, the first and second arms extending from the front piece to first and second earpieces, respectively, which are shaped to contact and rest, at least partly, on the ear of the patient, at least one of the earpieces carrying an earpiece electrode, the wearable device further including a control circuit and a power source, the control circuit configured to issue electrical signals through the front electrode or front electrode pad and the earpiece electrode to provide therapy to the eye of the patient, such that the nosepiece rests on the patient's nose and the first and second earpieces rest on the patient's ears, wherein the earpiece electrode is positioned on or behind the ear when the wearable device is worn by the user and the front electrode or front electrode pad is adjustably coupled to the front piece to be held against an upper eyelid of the user; and activating circuitry of the wearable device to deliver therapy via the at least one front electrode or electrode pad and the earpiece electrode.

16. A method of treating a patient comprising delivering a plurality of electrical pulses between a first electrode and a second electrode, wherein the first and second electrodes are part of a wearable device for providing therapy to the patient including a frame having a front piece and first and second arms extending therefrom, the front piece including a nosepiece and carrying the first electrode thereon, the first and second arms extending from the front piece to first and second earpieces, respectively, which are shaped to contact and rest, at least partly, on the ear of the patient, at least one of the earpieces carrying the second electrode in the form of an earpiece electrode, wherein the earpiece electrode is positioned on or behind the ear when the wearable device is worn by the user and the front electrode or front electrode pad is adjustably coupled to the front piece to be held against an upper eyelid of the user, the wearable device further including a control circuit and a power source, the control circuit configured to issue electrical signals through the first electrode and the second electrode to provide therapy to the eye of the patient.

* * * * *